US007301024B2

(12) United States Patent
Amir et al.

(10) Patent No.: US 7,301,024 B2
(45) Date of Patent: Nov. 27, 2007

(54) CRYSTALLINE FORMS OF GATIFLOXACIN AND PROCESSES FOR PREPARATION

(75) Inventors: Ehud Amir, Ramat-Aviv (IL); Valerie Niddam-Hildesheim, Kadima (IL); Greta Sterimbaum, Rishon-Lezion (IL); Shlomit Wizel, Petah Tiqva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 389 days.

(21) Appl. No.: 10/735,029

(22) Filed: Dec. 12, 2003

(65) Prior Publication Data

US 2004/0171621 A1    Sep. 2, 2004

Related U.S. Application Data

(60) Provisional application No. 60/465,534, filed on Apr. 25, 2003, provisional application No. 60/448,062, filed on Feb. 15, 2003, provisional application No. 60/432,961, filed on Dec. 12, 2002.

(51) Int. Cl.
*C07D 401/04* (2006.01)

(52) U.S. Cl. .................................................... 544/363
(58) Field of Classification Search .............. 544/363; 514/253.02
See application file for complete search history.

(56) References Cited

FOREIGN PATENT DOCUMENTS

| EP | 0 805 156 A | 11/1997 |
|---|---|---|
| WO | WO 02 22126 | 3/2002 |
| WO | WO 03 094919 | 11/2003 |

OTHER PUBLICATIONS

Polymorphism in Pharmaceutical Solids, Edited by Harry G. Brittain (1999).*

* cited by examiner

*Primary Examiner*—Johann Richter
*Assistant Examiner*—Ebenezer Sackey
(74) *Attorney, Agent, or Firm*—Kenyon & Kenyon LLP

(57) ABSTRACT

Provided are novel crystalline forms of gatifloxacin, some of which are DMSO solvates, and methods for making them.

3 Claims, 26 Drawing Sheets

CRYSTALLINE FORMS OF GATIFLOXACIN AND PROCESSES FOR PREPARATION

CROSS REFERENCE TO RELATED APPLICATIONS

This application claims the benefit of priority to U.S. provisional patent application Ser. Nos. 60/432,961, filed Dec. 12, 2002, 60/448,062, filed Feb. 15, 2003, and 60/465,534, filed Apr. 25, 2003, hereby incorporated by reference.

FIELD OF THE INVENTION

The present invention relates to novel forms of (±) 1-cyclopropyl-6-fluoro-1,4-dihydro-8-methoxy-7-(3-methyl-1-piperazinyl)-4-oxo-3-quinolinecarboxylic acid, commonly known as gatifloxacin. More specifically, the present invention relates to novel crystalline forms of gatifloxacin denominated form CW, CX, CY, CZ, W, X, Y, Z, CH1, CH2, RH, HX1, and HX2, several of which are DMSO solvates. The invention also relates to novel methods of making prior-art forms."

BACKGROUND OF THE INVENTION

Gatifloxacin, known as (±)-1-cyclopropyl-6-fluoro-1,4-dihydro-8-methoxy-7-(3-methyl-1-piperazinyl)-4-oxo-3-quinolinecarboxylic acid, has the following structure (I):

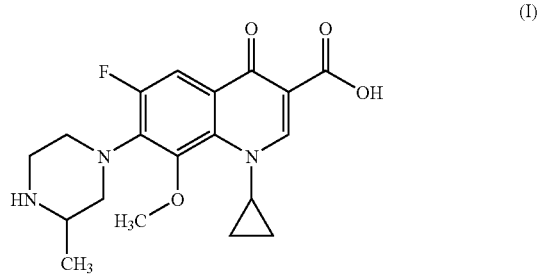

(I)

Gatifloxacin, an anti-bacterial agent, is marketed as Tequin® by BristolMyersSquibb®. Tequin® is available in a dosage of 200 mg and 400 mg in the form of a vial or a tablet, which can be either injected or taken orally.

Polymorphism and pseudopolymorphism are known in the pharmaceutical sciences. For a general review of polymorphs and the pharmaceutical applications of polymorphs see G. M. Wall, *Pharm Manuf.* 3, 33 (1986); J. K. Haleblian and W. McCrone, *J Pharm. Sci.*, 58, 911 (1969); and J. K. Haleblian, *J Pharm. Sci.*, 64, 1269 (1975), all of which are incorporated herein by reference. Thus, many pharmaceutically active organic compounds can crystallize in more than one type of molecular packing with more than one type of internal crystal lattice. The respective resulting crystal structures can have, for example, different unit cells. This phenomenon—identical chemical structure but different internal structure—is referred to as polymorphism and the species having different molecular structures are referred to as polymorphs.

Many pharmacologically active organic compounds can also crystallize such that second, foreign molecules, especially solvent molecules, are regularly incorporated into the crystal structure of the principal pharmacologically active compound. This phenomenon is referred to as pseudopolymorphism and the resulting structures as pseudopolymorphs. When the second molecule is a solvent molecule, the pseudopolymorphs can be referred to as solvates.

However, it is generally not possible to predict whether a particular organic compound will form polymorphs or pseudopolymorphs, let alone predict the structure and properties of the polymorphs or pseudopolymorphs.

The discovery of a new polymorph or pseudopolymorph of a pharmaceutically useful compound provides an opportunity to improve the performance characteristics of a pharmaceutical product. It enlarges the repertoire of materials that a formulation scientist has available for designing, for example, a pharmaceutical dosage form of a drug with a targeted release profile or other desired characteristic. It is clearly advantageous when this repertoire is enlarged by the discovery of new polymorphs or pseudopolymorphs of a useful compound.

Polymorphs and pseudopolymorphs are known to be influenced by controlling the conditions under which the compound is obtained in solid form. Solid state physical properties that can differ from one polymorph to the next include, for example, the flowability of the milled solid. Various polymorphs or pseudopolymorphs can be more or less hygroscopic. Absorption of atmospheric moisture by compound in powder form can impede its ability to flow. Flowability affects the ease with which the material is handled during processing into a pharmaceutical product. When particles of the powdered compound do not flow past each other easily, a formulation specialist must take that fact into account in developing a tablet or capsule formulation, which may necessitate the use of glidants such as colloidal silicon dioxide, talc, starch or tribasic calcium phosphate.

Another important solid state property of a pharmaceutical compound that is reported to vary from one polymorph or pseudopolymorph to the next is its rate of dissolution in aqueous media, e.g., gastric fluid. The rate of dissolution of an active ingredient in a patient's stomach fluid can have therapeutic consequences since it imposes an upper limit on the rate at which an orally-administered active ingredient can reach the patient's bloodstream. The rate of dissolution is also a consideration in formulating syrups, elixirs and other liquid medicaments. The solid state form of a compound may also affect its behavior on compaction and its storage stability.

These practical physical characteristics are said to be influenced by the conformation, orientation, and packing of molecules in the unit cell, which characterize a particular polymorphic or pseudopolymorphic form of a substance. A polymorphic form may have thermodynamic properties different from those of the amorphous material or another polymorphic form. Thermodynamic properties can be used to distinguish between various polymorphs or pseudopolymorphs. Thermodynamic properties that can be used to distinguish between polymorphs and pseudopolymorphs can be measured in the laboratory by such techniques as capillary melting point, thermogravimetric analysis (TGA), differential scanning calorimetry (DSC), and differential thermal analysis (DTA).

A particular polymorph or pseudopolymorph may also possess distinct spectroscopic properties that may be detectable by, for example, solid state $^{13}C$ NMR spectroscopy and infrared (IR) spectroscopy. This is particularly so in the case of pseudopolymorphs that are solvates because of the presence of absorptions or resonances due to the second, foreign molecule.

(±) 1-Cyclopropyl-6-fluoro-1,4-dihydro-8-methoxy-7-(3-methyl-1-piperazinyl)-4-oxo-3-quinolinecarboxylic acid, commonly known as gatifloxacin (gatifloxacin), is a synthetic broad-spectrum antibacterial agent for oral or intravenous administration. (See, e.g., *Physicians' Desk Reference*, 1110 (56$^{th}$ ed., 2002).)

U.S. Pat. No. 5,880,283 discloses that gatifloxacin forms a hygroscopic hemihydrate. The hemihydrate (a pseudopolymorph) is reported to be easily formed upon crystallization of gatifloxacin from water-containing organic solvents. The hemihydrate reportedly has disadvantages for manufacturing of solid oral dosage forms, e.g., tablets. The patent further discloses a novel pseudopolymorph of gatifloxacin, the sesquihydrate, and presents thermal analysis and x-ray diffraction data for this material. The sesquihydrate is reported to be less hygroscopic and more stable in manufacturing.

U.S. Pat. No. 6,413,969 discloses at least 12 different polymorphs or pseudopolymorphs of gatifloxacin and discloses the x-ray powder diffraction diagrams of at least 10 of these. The hexahydrate, pentahydrate and sesquihydrate are crystallized directly from aqueous solvents. Other crystalline forms are crystallized from a molten phase or by solid-solid phase transformations. The pentahydrate form is, according to the disclosure of U.S. Pat. No. 6,413,969, the most thermodynamically stable form and reportedly has the lowest aqueous solubility at room temperature. The interrelationships between the twelve identified crystalline forms are given in the application.

The present inventors are not aware of evidence in the literature as to the existence of anhydrous or solvated forms of gatifloxacin (other than the ethanolate).

SUMMARY OF THE INVENTION

In one aspect, the present invention relates to a crystalline DMSO solvate of gatifloxacin characterized by at least one characteristic selected from: x-ray reflections at about 14.7, 16.3, 17.6, and 19.7°±0.2° 2θ, and endothermic peaks at about 133° and about 167° C. in DSC. This crystalline form, denominated for CW, is further characterized by x-ray reflections at about 8.2, 13.1, 20.3, 21.2, and 23.0°±0.2° 2θ. Form CW has a DMSO content of about 20% to about 27% by weight.

In another aspect, the present invention relates to a method of making a crystalline form of gatifloxacin having at least one characteristic of form CW including the steps of: providing gatifloxacin form CX, and drying the gatifloxacin form CX at reduced pressure for about 8 hours to obtain the crystalline form having at least one characteristic of form CW.

In another aspect, the present invention relates to a crystalline form of gatifloxacin that is a DMSO solvate characterized by at least one characteristic selected from: x-ray reflections at about 6.5, 14.6, 17.4, and 19.4°±0.2° 2θ, and endothermic peaks at about 122° and about 137° in DSC. This crystalline form of gatifloxacin, denominated form CX, can be further characterized by x-ray reflections at about 6.5, 14.6, 17.4, and 19.4°±0.2° 2θ. Form CX has a DMSO content of about 25% to about 30% by weight In a further aspect, the present invention relates to a method of making a crystalline form of gatifloxacin having at least on characteristic of DMSO solvate form CX including the steps of: combining an initial solution of gatifloxacin in DMSO with water at a temperature of about 55° C., cooling the combination to a temperature of about 0° C. at a cooling rate of about 10° per hour whereby a suspension is obtained, isolating the crystalline form of gatifloxacin having at least one characteristic of form CX from the suspension, and washing the isolated crystalline form of gatifloxacin with sufficient acetonitrile to maintain the crystalline form as form CX.

In yet another aspect, the present invention relates to a crystalline form of gatifloxacin characterized by at least one of: x-ray reflections at about 5.2, 11.2, 11.5, 14.3, and 22.2°±0.2° 2θ, and an endothermic peak at about 178° C. in DSC. This crystalline form of gatifloxacin, denominated form CY, can be further characterized by x-ray reflections at about 15.5, 16.2, 16.5, 17.0, 17.5, 20.4, and 23.2°±0.2° 2θ.

In another aspect, the present invention relates to method of making a crystalline form of gatifloxacin having at least one characteristic of form CY including the steps of: providing an initial solution of gatifloxacin in DMSO at a concentration of at least about 2 M and a temperature of about 40° C., combining the solution with water at a temperature of about 40° C., cooling the solution to a temperature of about 5° C. and maintaining the suspension obtained at about 5° C. for a holding time, isolating DMSO-wet solid gatifloxacin from the suspension, suspending the isolated DMSO-wet solid gatifloxacin in acetonitrile, isolating the gatifloxacin from the suspension, and drying the isolated gatifloxacin at about 50° C. and reduced pressure for at least about 12 hours.

In a further aspect, the present invention relates to a crystalline form of gatifloxacin characterized by at least one of: x-ray reflections at about 6.6, 7.2, 13.2, 17.6, 19.8, and 23.0°±0.2° 2θ, and an endotherm at about 122° C. in DSC. This form is denominated form CZ.

In another aspect, the present invention relates to a method of making a crystalline form having at least one characteristic of form CZ including the steps of: providing an initial solution of gatifloxacin in DMSO at about 55° C., combining, at about 55° C., the provided solution with water and toluene, 1:2 to 1:3, vol:vol, cooling the resulting mixture to about 11° C. at a cooling rate of about 10° per hour, heating the mixture to about 35° C. and maintaining the mixture at this temperature for about 1 hour, cooling the mixture to about 11° C. at a cooling rate of about 4° per hour, maintaining the resulting suspension at about 10° C. for a holding time, isolating the gatifloxacin having at least one characteristic of form CZ from the suspension obtained, and washing the isolated gatifloxacin with acetonitrile.

In another aspect, the present invention relates to a crystalline form of gatifloxacin characterized by at least one of: x-ray reflections at about 7.8, 10.8, 13.7, 18.6, and 19.9°±0.2° 2θ, and endotherms at about 90° and about 175° C. in DSC. This crystalline form is designated as form W.

In yet another aspect, the present invention relates to a method of making a crystalline form of gatifloxacin having at least one characteristic of form W including the steps of: providing, at reflux temperature, a solution of gatifloxacin in acetonitrile, combining, at reflux temperature, the solution with about one-tenth of its volume of polyethylene glycol, cooling the resulting solution to about 57° C. and seeding the solution with gatifloxacin hemihydrate, maintaining the seeded solution at about 57° C. for about 2 hours, cooling the resulting seeded solution to about 5° C. at about 5° per hour, maintaining the resulting suspension at about 5° C. for a holding time, isolating crystalline gatifloxacin the suspension, washing the isolated crystalline gatifloxacin with acetonitrile, and drying the isolated, acetonitrile-washed crystalline gatifloxacin to obtain gatifloxacin having at least one characteristic of form W.

In still yet a further aspect, the present invention relates to a crystalline form of gatifloxacin characterized by at least one of: x-ray reflections at about 13.4, 14.8, 17.6, 19.6, and 20.0°±0.2° 2θ, and an endotherm at about 99° C. in DSC. This crystalline form is denominated form X.

In another aspect, the present invention relates to a crystalline form of gatifloxacin characterized by at least one of: x-ray reflections at about 13.9, 14.8, and 16.1°±0.2° 2θ, and endotherms at about 92° and about 188° C. in DSC. This crystalline form is denominated form Y.

In a further aspect, the present invention relates to a method of making a crystalline form of gatifloxacin having at least one characteristic of form Y including the steps of: providing a slurry of gatifloxacin hydrochloride in a 9:1, vol:vol, mixture of acetonitrile and water at a temperature of about 5° C., combining the suspension with a volume of an aqueous solution of NaOH sufficient to neutralize at least about 70 mole % of the hydrochloride, isolating solid gatifloxacin from the resulting suspension, washing the isolated solid gatifloxacin with a 9:1, v:v mixture of acetonitrile and water, and drying the isolated solid gatifloxacin at about 50° C. and reduced pressure to obtain the crystalline form of gatifloxacin having at least one characteristic of form Y.

In another aspect, the present invention relates to a crystalline form of gatifloxacin having at least one characteristic selected from: x-ray reflections at about 6.7, 9.5, 10.7, 13.1, 17.2°±0.2° 2θ, and endotherms at about 65°, 90°, and 190° C. in DSC, wherein the endotherm at 190° C. is sharper than the other endotherms. This crystalline form is denominated form Z.

In another aspect, the present invention relates to a method of making a crystalline form of gatifloxacin having at least one characteristic of form Z including the steps of: providing a hot-filtered solution of gatifloxacin in acetonitrile at about 80° C., cooling the solution to about 60° C., maintaining the filtered solution at about 60° C. for about 1 hour, cooling the solution to about 5° C. at a cooling rate of about 20° to about 25° per hour, maintaining the resulting suspension at about 5° C. for about 30 minutes, isolating the crystalline form of gatifloxacin having at least one characteristic of form Z from the suspension.

In another aspect, the present invention relates to a method of making a novel form of gatifloxacin, denominated form CH1, characterized by x-ray reflections at about 5.5, 10.3, 10.8, 13.9, and 15.1°±0.2° 2θ. Form CH1 can be made by heating form CY at about 100° C. for at least about 30 minutes.

In still a further aspect, the present invention relates to a novel crystalline form of gatifloxacin, denominated form CH2, characterized by x-ray reflections at about 7.8, 9.1, 9.4, and 9.6°±0/2° 2θ.

In another aspect, the present invention relates to a novel crystalline form of gatifloxacin, denominated form RH, characterized by x-ray reflections at about 6.6, 9.9, 10, 5, and 12.9°±0.2° 2θ. Form RH can be made by, for example, heating form R.

In still yet another aspect, the present invention relates to a novel crystalline form of gatifloxacin, denominated HX1, characterized by x-ray reflections at about 6.3, 9.3, 19.3, 20.8, 24.5, and 25.1°±0.2° 2θ0.

In another aspect, the present invention relates to a novel crystalline form of gatifloxacin, denominated form HX2, characterized by x-ray reflections at 6.4, 9.4, 16.4, 18.9, and 19.2°±0.2° 2.

In still yet another aspect, the present invention relates to pharmaceutical compositions containing at least one pharmaceutically acceptable excipient and at least one crystalline form of gatifloxacin having at least one characteristic of forms CW, CX, CY, CZ, W, X, Y, X, CH1, CH2, RH, HX1, of HX2.

DETAILED DESCRIPTION OF THE INVENTION

Figure 1:
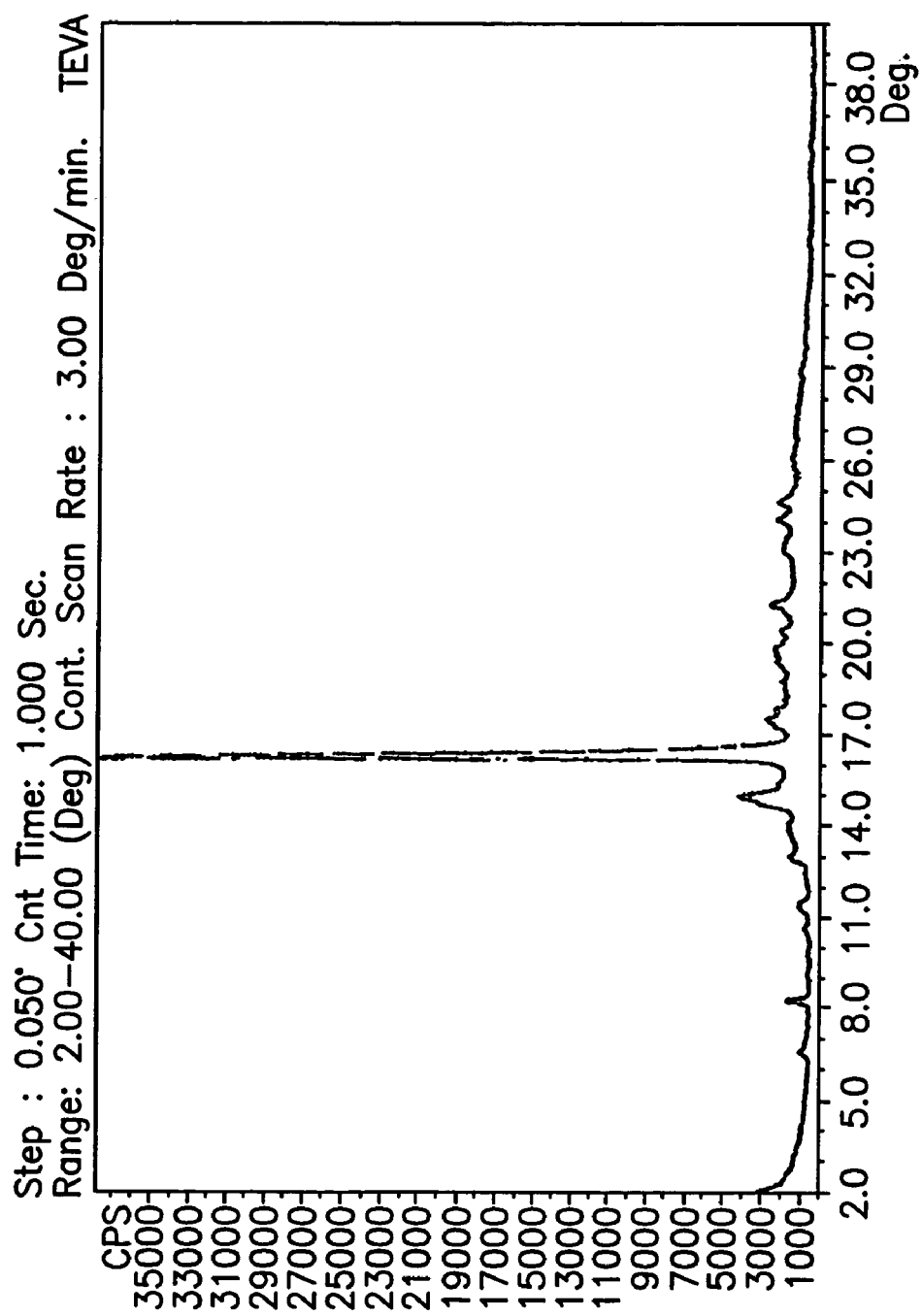
FIG. 1 is a representative x-ray diffraction diagram of gatifloxacin form CW.

The present invention provides thirteen novel crystalline forms of gatifloxacin, denominated form CW, CX, CY, CZ, W, X, Y, Z, CH1, CH2, RH, HX1 and HX2, respectively, several of which are solvates, and methods for making them.

As used herein in connection with a measured quantity, the term, "about," refers to that variation in the measured quantity as would be expected by the skilled artisan making the measurement and exercising a level of care commensurate with the objective of the measurement and the precision of the measuring equipment used.

As used herein, unless otherwise qualified, gatifloxacin refers to gatifloxacin in any crystalline form (polymorph or pseudopolymorph), or in the amorphous state.

As used herein, gatifloxacin hydrochloride refers to the hydrochloride salt of gatifloxacin and can be from any source.

As used herein, the abbreviation DMSO refers to the chemical compound dimethylsulfoxide.

As used herein in connection with gatifloxacin or any crystalline form thereof, water content refers to wt-% water as determined by the Karl Fisher method.

As used herein, the term "gatifloxacin hemihydrate" refers to the crystalline form disclosed under such designation in U.S. Pat. No. 5,880,283.

As used herein, the terms "gatifloxacin pentahydrate", form "omega" (Ω), and form "T2RP" refer to the crystalline forms of gatifloxacin disclosed under such names in U.S. Pat. No. 6,413,969.

As used herein "gatifloxacin hydrochloride" represents the hydrochloride salt of gatifloxacin.

As used herein, the term ambient temperature is a temperature between about 18° and about 30° C.

As used herein in connection with drying or otherwise treating a solid, the term reduced pressure refers to a pressure of about 50 to about 500 mm Hg.

As used herein, LOD refers to loss-on-drying as determined by TGA.

As used herein in connection with a crystalline form of gatifloxacin, the term DMSO content refers to weight percent DMSO.

As used herein in connection with a combination or mixture of liquids, the expressions v/v and v:v are synonymous and refer to the ratio of the volumes of the liquids used to form the combination or mixture. Thus, 1/1, v/v; 50/50, v/v; and 50:50, v:v all refer to a mixture or combination of equal volumes of two liquids; 1:2, v:v, denotes a mixture of one volume of a first liquid with 2 like volumes of a second liquid; and so forth.

As used in connection with the present invention, x-ray diffraction refers to x-ray diffraction by the powder diffraction technique (PXRD). X-ray powder diffraction analysis was performed using a Scintag powder diffractometer with variable goniometer, a Cu source, and a solid state detector. A standard round aluminum sample holder with zero background quartz plate was used. Samples were scanned from 2° to 40° 2θ at 3° per minute. Reflections are reported as peak maxima in the Intensity vs. 2θ plots, and are subject to the normal experimental error (uncertainty). Wet samples were promptly analyzed "as is," i.e., without drying or grinding prior to the analysis.

Differential scanning calorimetric (DSC) analysis was performed with a Mettler Toledo DSC 821$^e$ calorimeter. Samples of about 3 to about 5 milligrams, held in a vented (3-hole) crucible, were analyzed at a heating rate of 10° per minute.

Thermogravimetric analysis (TGA) was performed using a Mettler TG50 thermobalance. Samples of 7 to 15 milligrams were analyzed at a heating rate of 10° C. per minute in the temperature range between about 25° C. and about 200° C.

As used herein, the term gatifloxacin (or GTF) form '#'," where '#' is one or more letters or a letter and Arabic numeral (e.g., form X, form B1, form CZ, etc.), refers to a crystalline form of gatifloxacin that one of skill in the art can identify as a distinct crystalline form, distinguishable from other crystalline forms of gatifloxacin based on the characteristics of the crystalline form provided herein or in the literature.

As used herein, the phrase, "having at least one characteristic of gatifloxacin form '#'," where "#" is one or more letters or a letter and Arabic numeral (e.g., form X, form B1, form CZ, etc.), refers to a crystalline form of gatifloxacin that exhibits at least the characteristic powder x-ray diffraction (PXRD) reflections (or peaks), the characteristic FTIR absirption bands, or the characteristic DSC exotherms of form '#'.

Some processes of the present invention involve crystallization out of a particular solvent. One skilled in the art knows that some of the conditions concerning crystallization can be modified without affecting the form of the polymorph obtained. For example, when mixing gatifloxacin in a solvent to form a solution, warming of the mixture can be necessary to completely dissolve the starting material. If warming does not clarify the mixture, the mixture can be diluted or filtered. To filter, the hot mixture can be passed through paper, glass fiber or other membrane material, or a known filtering aid (clarifying agent) such as celite can be used.

In many embodiments of the present invention, a solid is isolated (recovered) from a slurry or suspension. In such cases the isolating can be by any means known in the art, for example filtration (gravity or suction) or centrifugation and decanting, to mention just three.

In one embodiment, the present invention provides a novel crystalline form of gatifloxacin that is a DMSO solvate, denominated form CW, and methods for making it.

One characteristic of form CW is its x-ray diffraction diagram. Form CW can be characterized by x-ray reflections at about 14.7°, 16.3°, 17.6°, and 19.7°±0,2° θ; and can be further characterized by x-ray reflections at 8,2°, 13.1°, 20.3°, 21.2°, 23.0°, 24.0°, and 24.5°±0.2° 2θ. A typical x-ray diffraction diagram of form CW is shown in FIG. 1.

Figure 14:
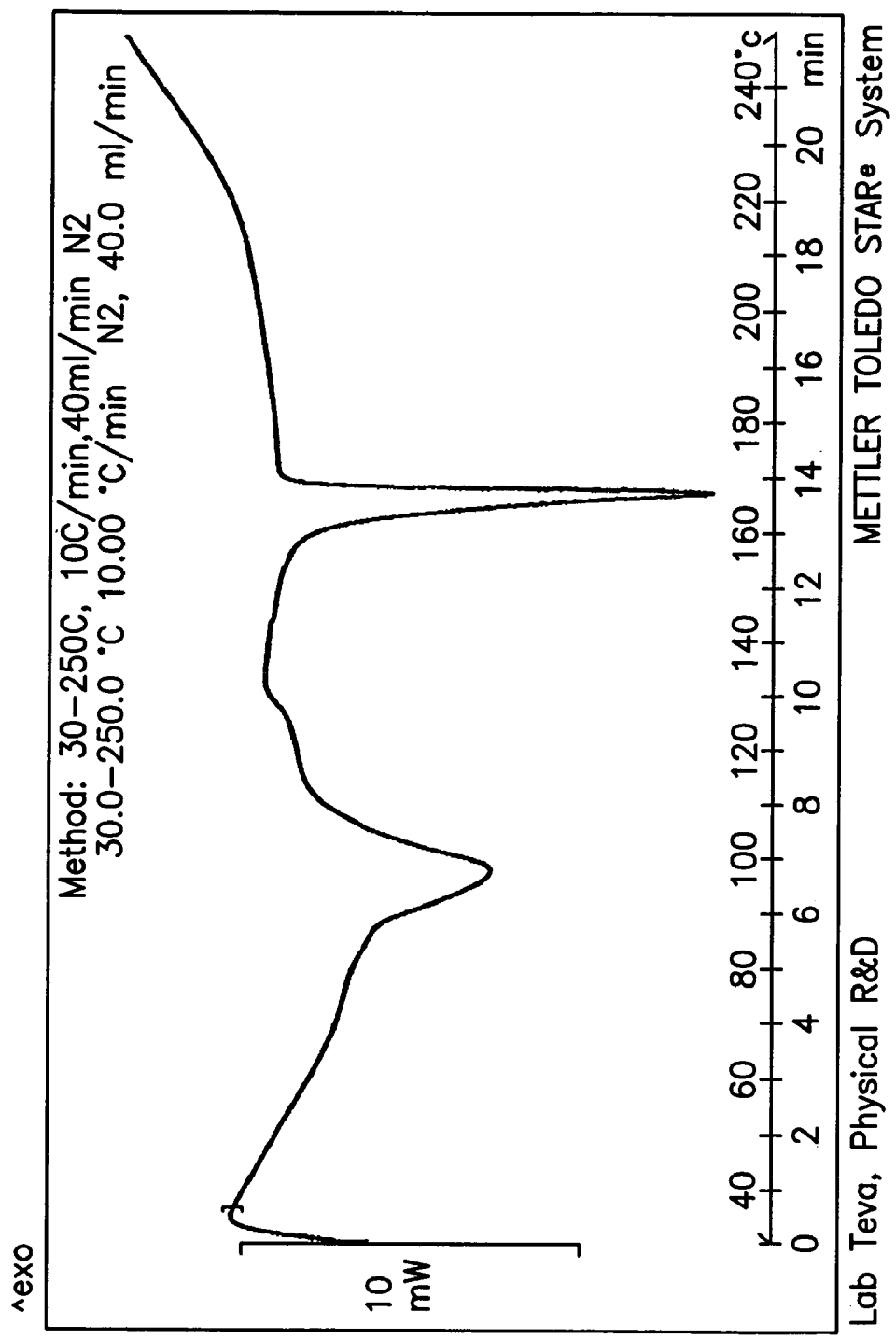
FIG. 14 is a representative DSC thermogram of gatifloxacin form CW.

Another characteristic of form CW is the endotherms observed in the DSC thermogram. A typical DSC thermogram of form CW is shown in FIG. 14. The DSC thermogram exhibits an endothermic peak at 167° C. and an additional endothermic peak at 133° C.

Figure 17:
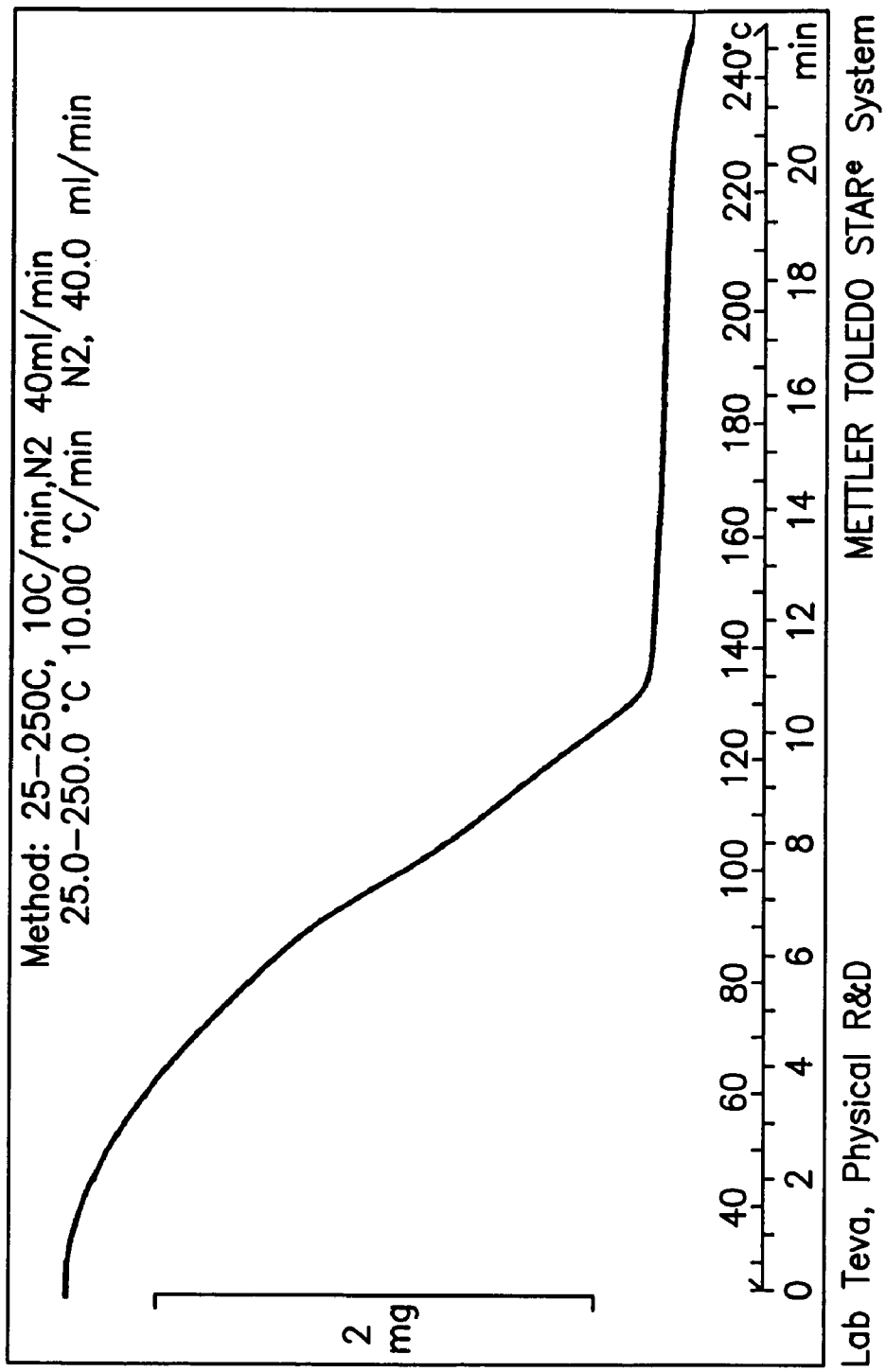
FIG. 17 is a representative TGA thermogram of gatifloxacin form CW.

Thermogravimetric analysis can also be applied to the characterization of form CW. The TGA plot for form CW is shown in FIG. 17. The loss on drying of form CW is typically about 30%.

Form CW can be obtained by, for example, drying form CX under vacuum at about 50° C.

In another embodiment, the present invention provides a novel crystalline form of gatifloxacin that is a DMSO solvate, denominated form CX, and methods for making it.

Figure 2:
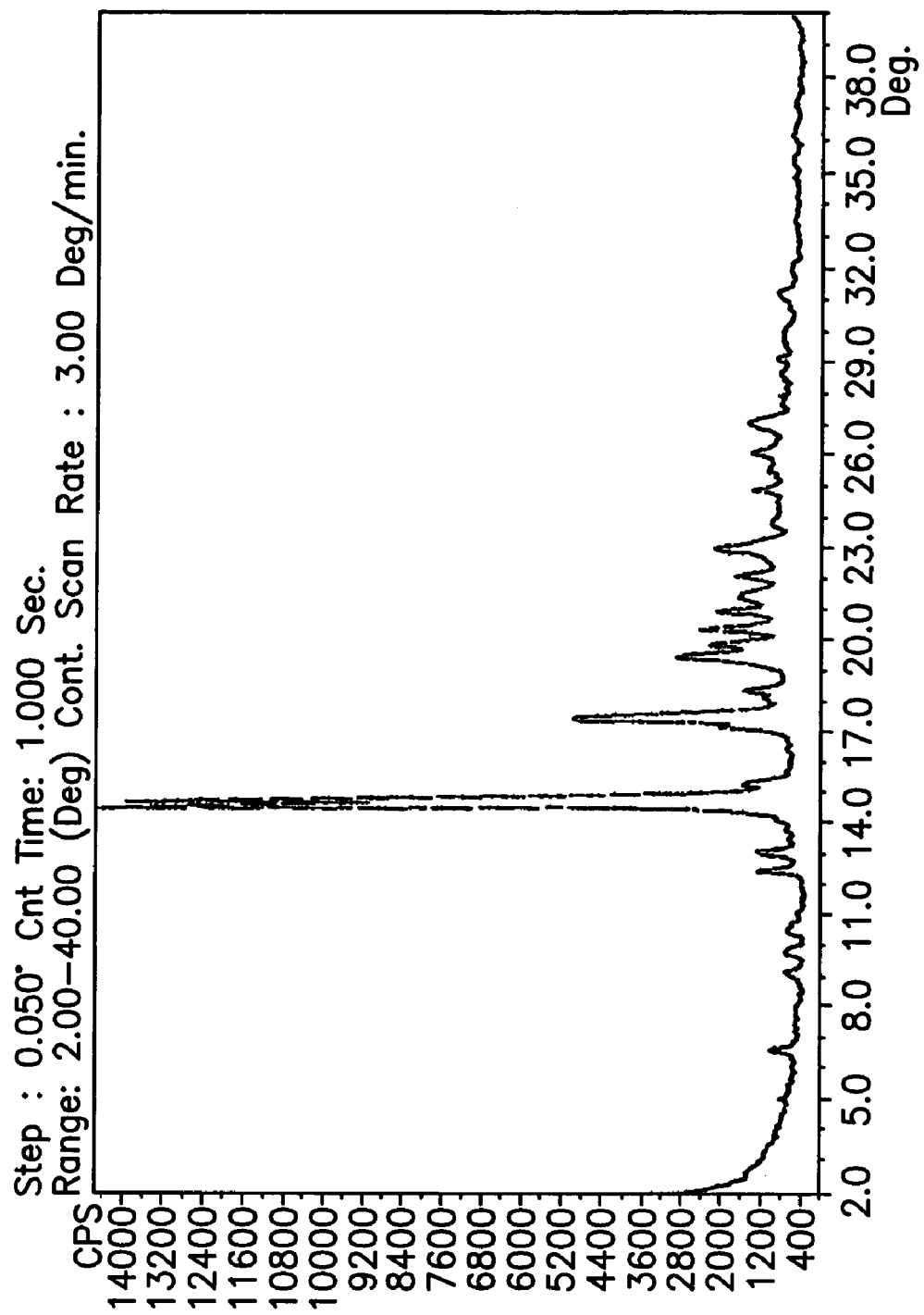
FIG. 2 is a representative x-ray diffraction diagram of gatifloxacin form CX.

One characteristic of form CX is its x-ray diffraction pattern. Form CX is characterized by x-ray reflections at about 6.5°, 14.6°, 17.4°, and 19.4°±0.2° 2θ and further characterized by x-ray reflections at 9.1°, 9.7°, 10.5°, 12.3°, 12.8°, 15.3°, 18.2°, 19.9°, 20.3°, 20.9°, and 23.0°±0.2° 2θ. A typical x-ray diffraction diagram of form CX, obtained on "as is" sample is shown in FIG. 2.

Figure 15:
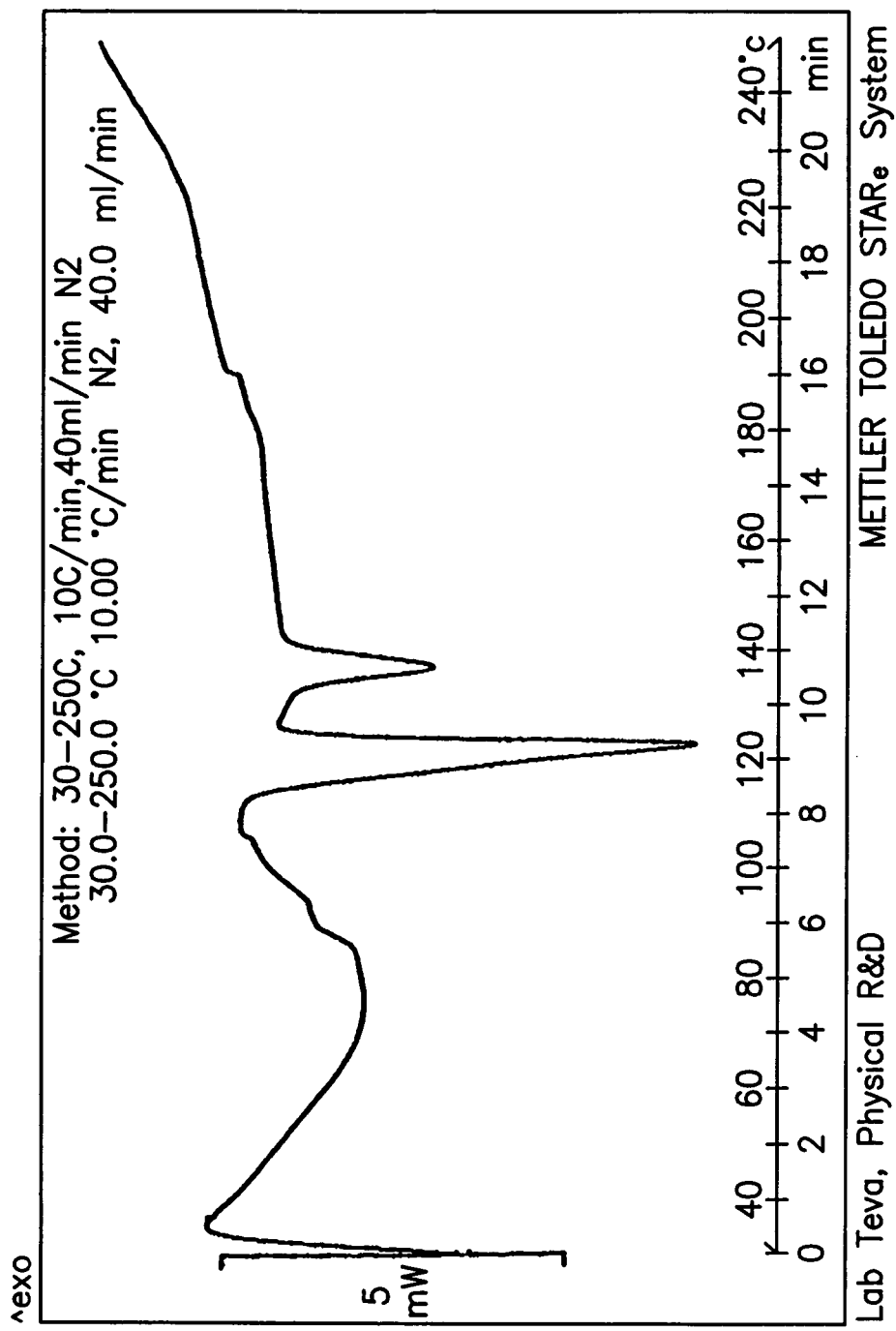
FIG. 15 is a representative DSC thermogram of gatifloxacin form CX.

Another characteristic of form CX is the pattern of endotherms observed in the DSC thermogram of form X. A typical DSC thermogram of form CX is shown in FIG. 15.

The DSC thermogram of form CX is characterized by endotherms having peaks at about 122° C. and about 137° C.

Figure 18:
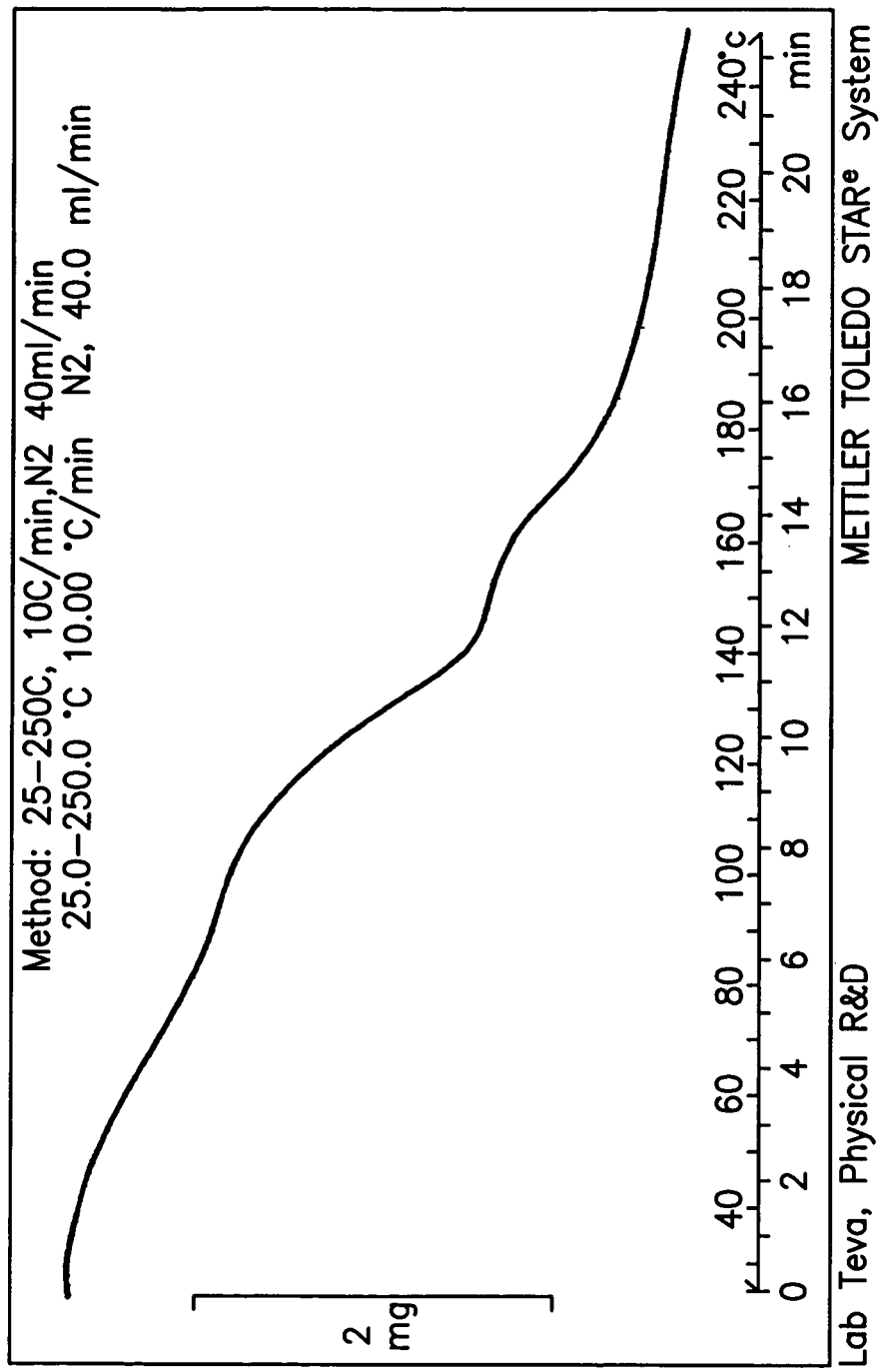
FIG. 18 is a representative TGA thermogram of gatifloxacin form CX.

Thermogravimetric analysis can also be applied to the characterization of form CX. The TGA plot for form CX is shown in FIG. 18. The TGA plot shows three weight-loss steps in the range of 30° to 220° C. (total loss on drying about 30%). Form CX is a DMSO solvate.

Form CX can be obtained in a process that includes the steps of combining, at about 55° C., an initial solution of gatifloxacin in DMSO (preferably but not necessarily about 1 to about 1.5 M) with water. The initial solution can be provided by any means or from any source. For example, an initial solution can be obtained by making gatifloxacin directly in DMSO as described below, in which case the final reaction mixture concentrated, if necessary, is an initial solution. The combination of initial DMSO solution and water is cooled at about 10° C. per hour to about 0° C., whereby a suspension is obtained. Form CX is isolated from the suspension. Form CX isolated "as is" is an example of a DMSO-wet gatifloxacin, useful in other embodiments of the present invention.

Form CX can be obtained in a direct process including the steps of synthesizing gatifloxacin from 2-methylpiperazine and 1-cyclopropyl-6,7-difluoro-1,4-dihydro-8-methoxy-4-oxo-3-quinolinecarboxylic acid in solution in DMSO solvent; diluting the final reaction mixture with water, cooling the diluted reaction mixture, and isolating form CX from the cooled, diluted reaction mixture. Form CX so made is a DMSO solvate.

The final reaction mixture is combined with about 15% to about 25%, preferably about 20%, of its volume of water. The diluted final reaction mixture is cooled to a temperature of about 0° C. Preferably, the cooling is at a rate of about 10° per hour.

In another embodiment, the present invention provides a novel crystalline form of gatifloxacin, denominated form CY, and methods for making it.

Figure 3:
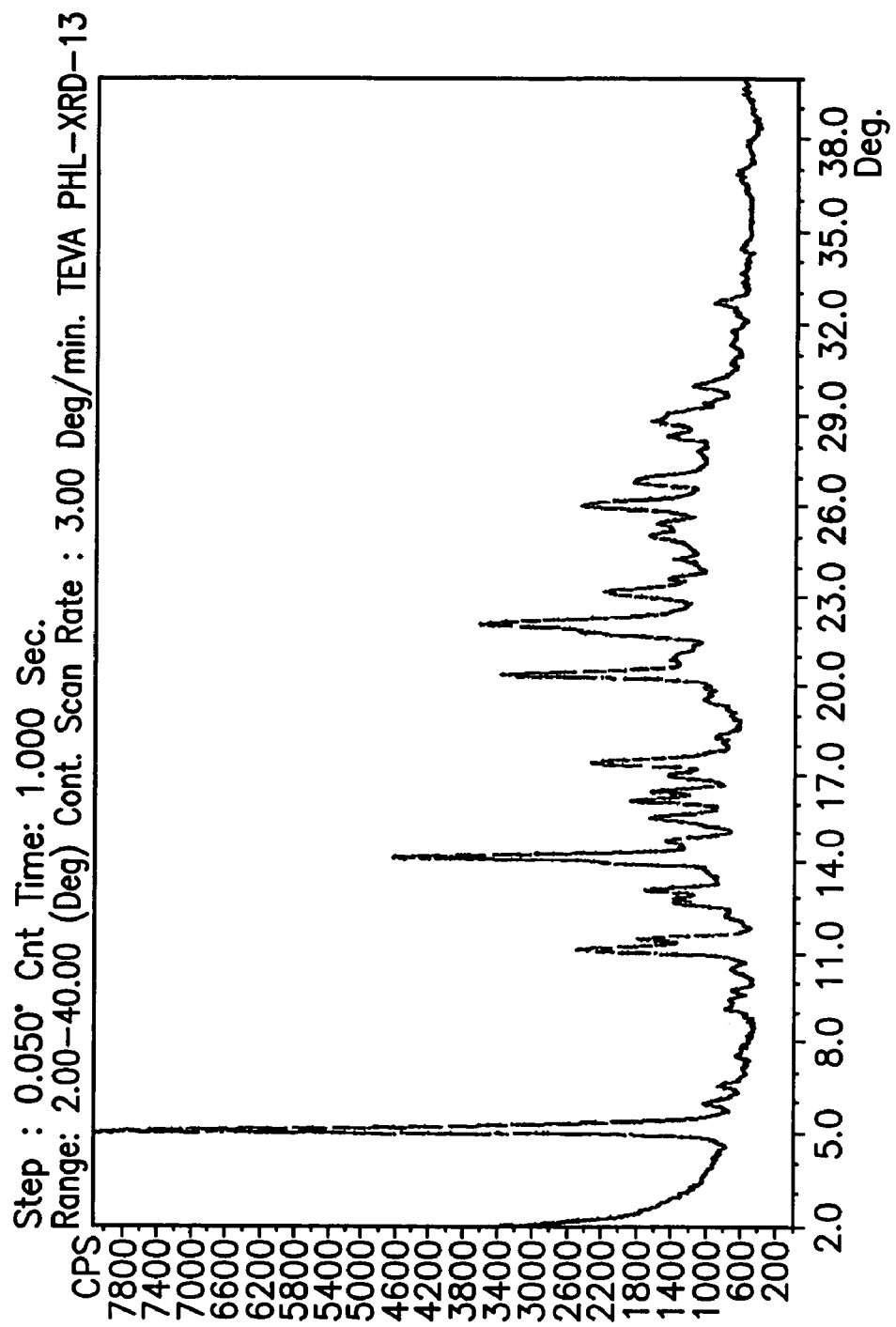
FIG. 3 is a representative x-ray diffraction diagram of gatifloxacin form CY.

One characteristic of form CY is its x-ray diffraction pattern. Form CY is characterized by x-ray reflections at about 5.2°, 11.2°, 11.5°, 14.3°, and 22.2°±0.2° 2θ; and further characterized by reflections at about 15.5°, 16.2°, 16.5°, 17.0°, 17.5°, 20.4° and 23.2°±0.2° 2θ. A typical x-ray diffraction diagram for form CY is shown in FIG. 3.

Figure 16:
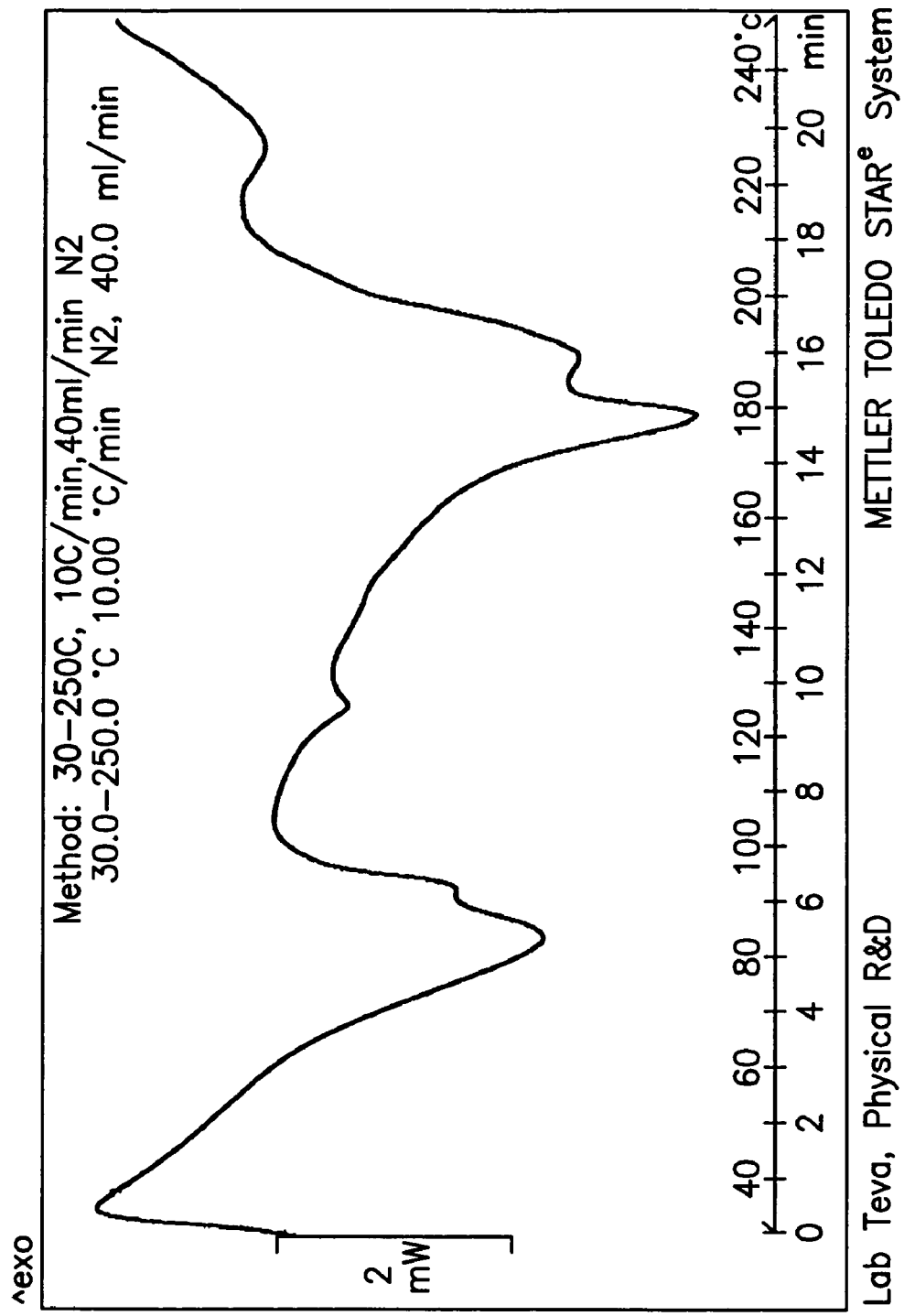
FIG. 16 is a representative DSC thermogram of gatifloxacin form CY.

Another characteristic of form CY is the endothermic peak observed in its DSC thermogram. A typical DSC thermogram of form CY is shown in FIG. 16. The DSC thermogram of form CY is characterized by an endothermic peak at about 178° C.

Figure 19:
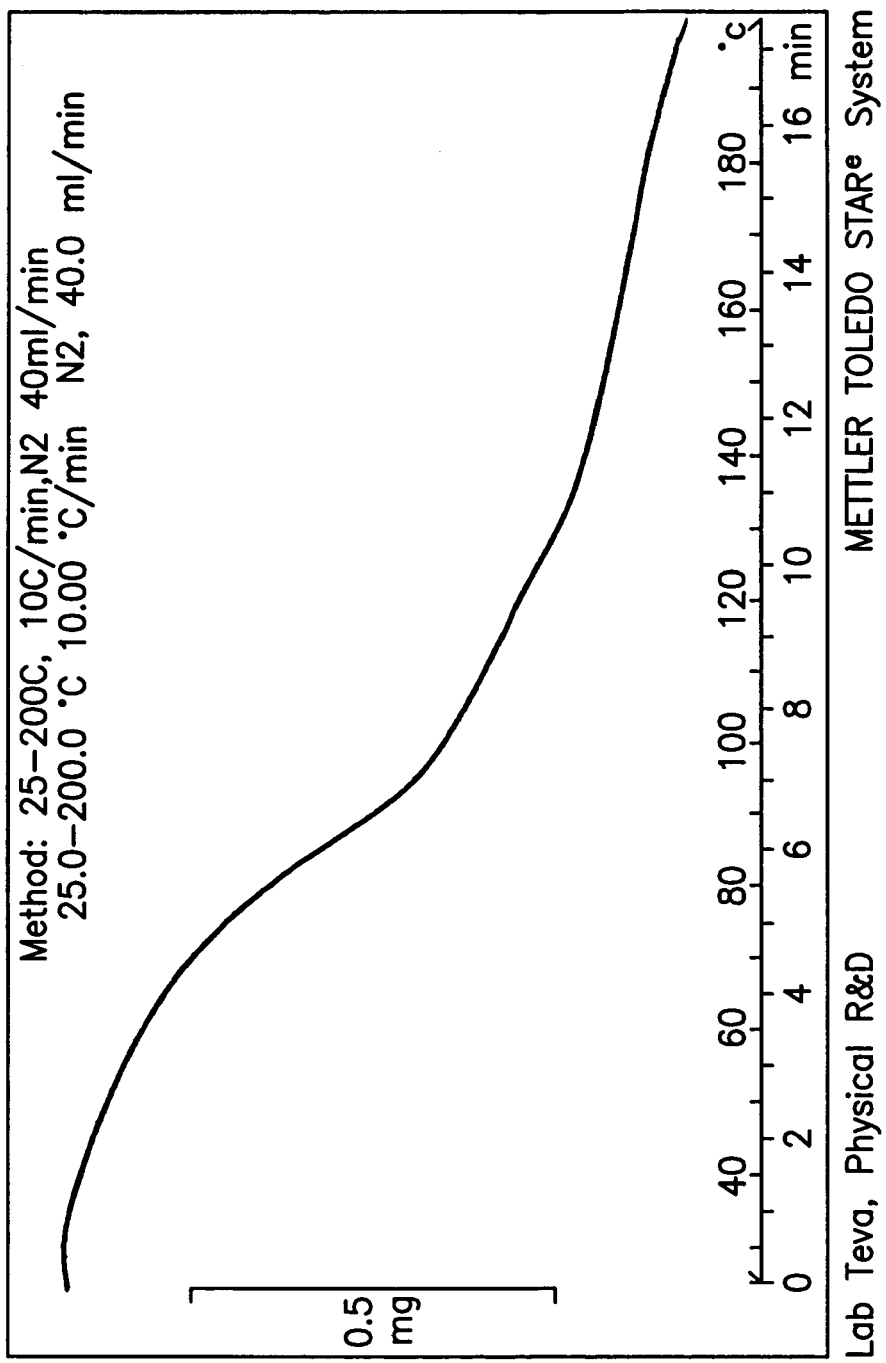
FIG. 19 is a representative TGA thermogram of gatifloxacin form CY.

Thermogravimetric analysis can also be applied to characterization of form CY. A typical TGA plot for form CY is shown in FIG. 19. Form CY shows a loss on drying of about 8% to about 9% in the range of 30° C. to 170° C.

Form CY can be obtained in a process that includes the steps of: providing an initial solution of gatifloxacin in DMSO at a concentration of at least about 2 M and a temperature of about 40° C., combining the initial solution with water at a temperature of about 40° C., cooling the solution to a temperature of about 50° C. and maintaining the suspension obtained at about 50@ C for a holding time, isolating DMSO-wet solid gatifloxacin from the suspension, suspending the isolated DMSO-wet solid gatifloxacin in acetonitrile, isolating the gatifloxacin from the suspension, and drying the isolated gatifloxacin at about 50° C. and reduced pressure for at least about 12 hours. The initial solution can be provided by any means, as discussed above.

In a preferred embodiment, form CY is obtained in a process that uses an initial solution made be the steps of synthesizing gatifloxacin from 2-methylpiperazine and 1-cyclopropyl-6,7-difluoro-1,4-dihydro-8-methoxy-4-oxo-3-quinolinecarboxylic acid in solution in DMSO solvent; concentrating the final reaction mixture by distilling-off DMSO solvent under high vacuum (<50 mm Hg); diluting the concentrated reaction solution with water; cooling the diluted reaction mixture; recovering the solid from the resulting suspension; suspending the recovered solid in acetonitrile, recovering the solid from the suspension, and drying the recovered solid to obtain form CY.

The initial reaction mixture is concentrated to about 25% of its initial volume by distilling-off DMSO under high vacuum especially at <50 mm Hg, most especially <5 mm Hg. The volume of water used to dilute the concentrated reaction mixture is approximately equal to the volume of the remaining concentrated reaction mixture.

Cooling of the diluted concentrated reaction mixture is to a temperature of about 5° C. Preferably, the cooled diluted mixture is held a about 5° C. for about 20 hours before the solid is recovered from the suspension. Drying of the recovered solid can be carried out at 50° C., preferably under vacuum.

In still a further embodiment, the present invention provides a novel crystalline form of gatifloxacin that is a DMSO solvate, denominated from CZ, and methods for making it.

Figure 4:
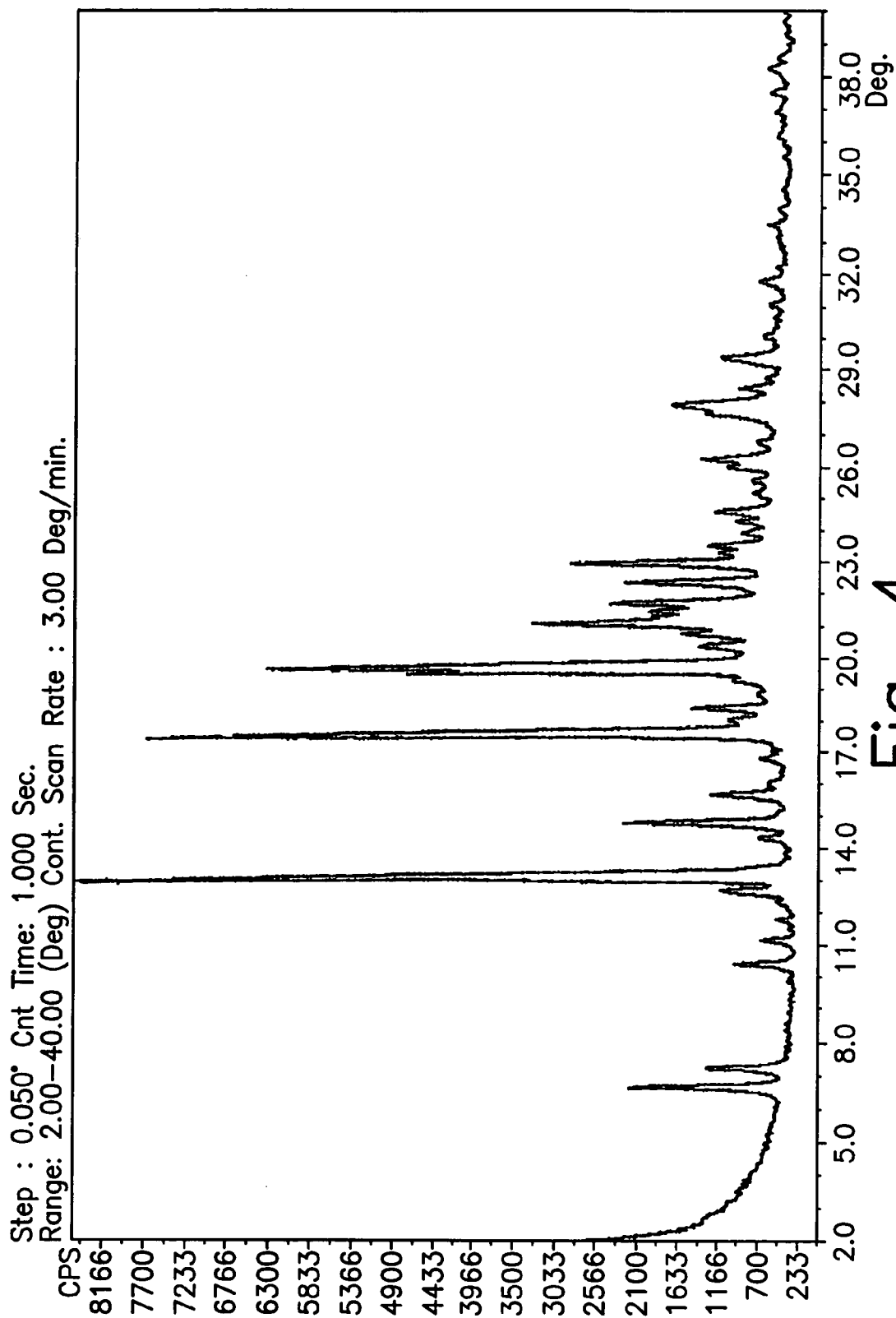
FIG. 4 is a representative x-ray diffraction diagram of gatifloxacin form CZ.

One characteristic of gatifloxacin form CZ is its powder x-ray diffraction pattern. Gatifloxacin form CZ is characterized by x-ray reflections at about 6.6°, 7.2°, 13.2°, 17.6°, 19.8°, and 23.0°, ±0.2° 2θ. A typical x-ray diffraction diagram of form CZ, obtained on "as is" sample, is shown in FIG. 4.

Figure 20:
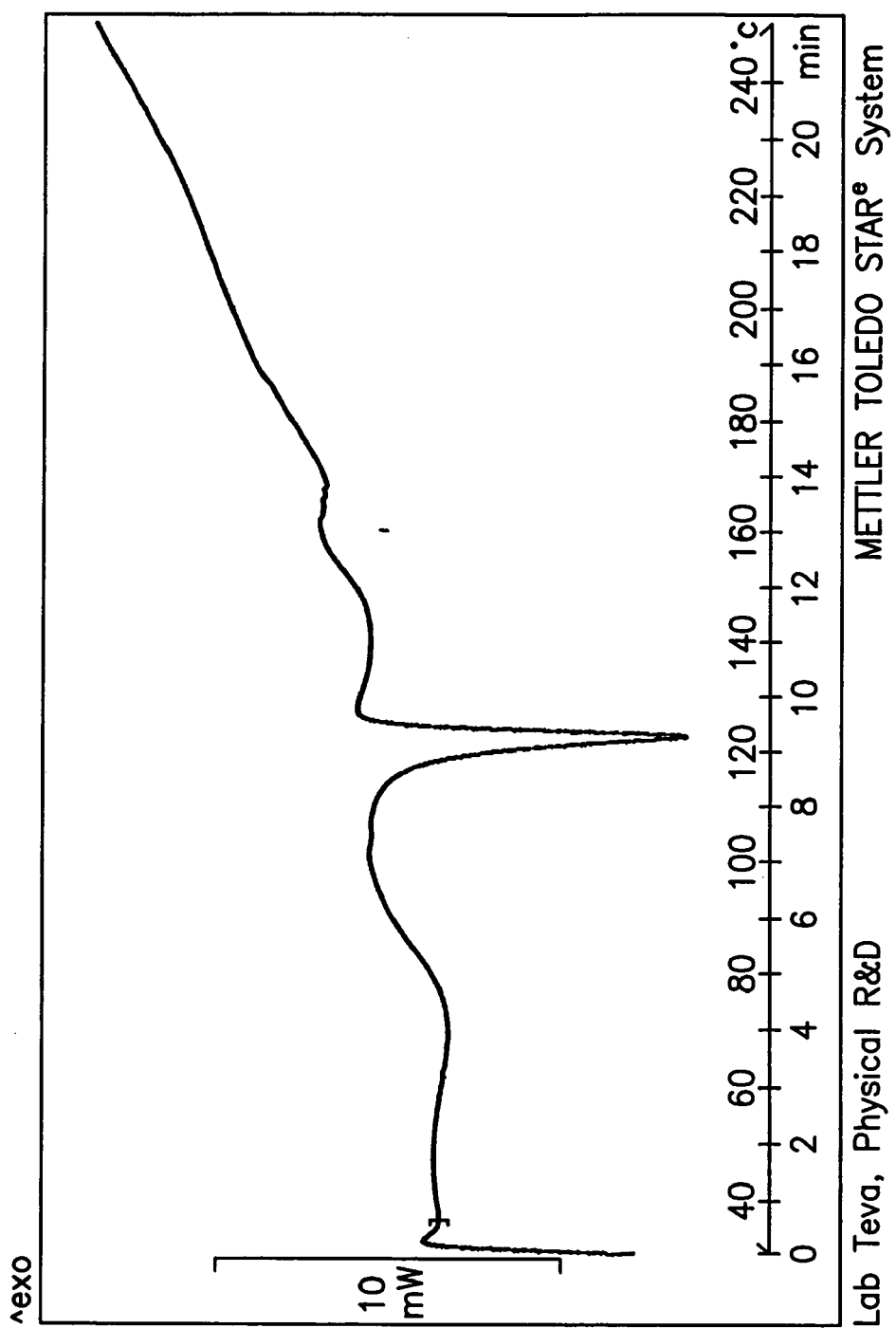
FIG. 20 is a representative DSC thermogram of gatifloxacin form CZ.

Another characteristic of gatifloxacin form CZ is the endotherm observed in differential scanning calorimetry (DSC). A typical DSC thermogram of gatifloxacin form CZ is shown in FIG. 20. The DSC thermogram of gatifloxacin form CZ is characterized by an endothermic peak at about 122° C.

Thermogravimetric analysis (TGA) can also be applied to further characterize gatifloxacin form CZ by a loss-on-drying (LOD) of about 30 wt-% in the temperature range between about 25° C. and about 200° C. Gatifloxacin form CZ is a DMSO solvate.

Form CZ DMSO solvate can be made in a process that includes the steps of: providing an initial solution of gatifloxacin in DMSO at about 55° C., combining, at about 55° C., the provided solution with water and toluene, 1:2 to 1:3, vol:vol, cooling the resulting mixture to about 10° C. at a cooling rate of about 10° per hour, heating the mixture to about 35° C. and maintaining the mixture at this temperature for about 1 hour, cooling the mixture to about 10° C. at a cooling rate of about 4° per hour, maintaining the resulting suspension at about 10√ C. for a holding time, preferably about 12 hours, and isolating the gatifloxacin having at least one characteristic of form CZ from the suspension obtained. Preferably, the isolated solid is washed with acetonitrile In a preferred embodiment, the present invention relates to a method of directly obtaining gatifloxacin form CZ comprising the steps of synthesizing gatifloxacin from 2-methylpiperazine and 1-cyclopropyl-6,7-difluoro-1,4-dihydro-8-methoxy-4-oxo-3-quinolinecarboxylic acid in solution in DMSO by heating to about 55° C. under nitrogen atmosphere, optionally maintaining the resulting mixture at a temperature of about 55° C. for a holding time; diluting the reaction mixture with ⅓ total starting volume of 2.5 parts toluene: 1 part water; cooling the diluted reaction mixture to a temperature of about 11° C., preferably at a cooling rate of about 11° C. per hour; optionally maintaining the resulting mixture at a temperature of about 11° C. for a holding time; heating the reaction mixture to a temperature of about 35° C., preferably at a heating rate of about 24° C. per hour; optionally maintaining the resulting mixture at a temperature of about 35° C. for a holding time; cooling the diluted reaction mixture to a temperature of about 11° C., preferably at a cooling rate of about 4° C. per hour; optionally maintaining the resulting mixture at a temperature of about 11° C. for a holding time; and recovering gatifloxacin form CZ from the resulting suspension by vacuum filtration and washing with acetonitrile. gatifloxacin form CZ so made is a DMSO solvate.

Form CZ van be converted to form V by heating at about 100° to about 130° C., especially at about 100° C.

In another embodiment, the present invention provides a novel crystalline form of gatifloxacin, denominated form W, and methods of making it.

Figure 5:
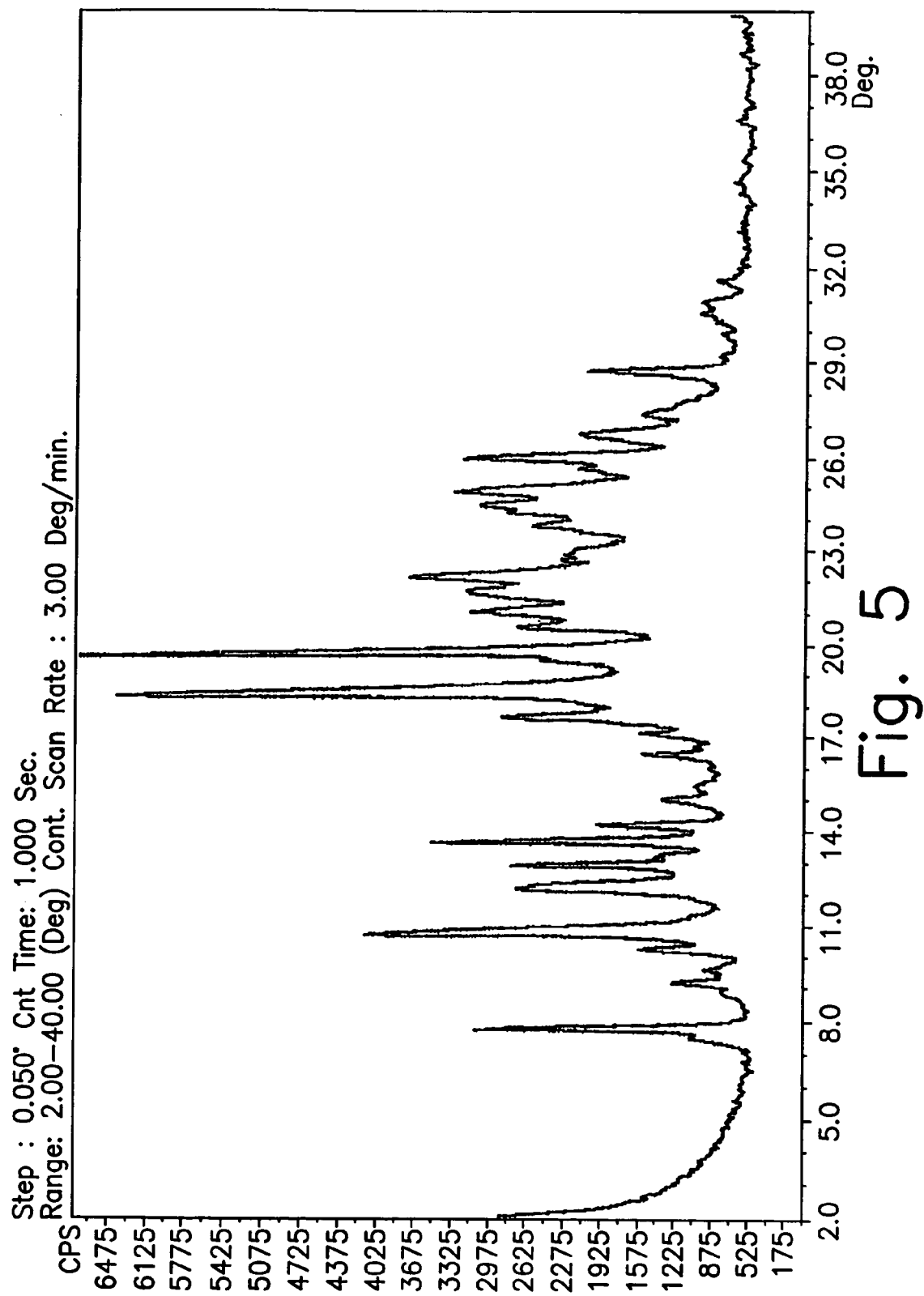
FIG. 5 is a representative x-ray diffraction diagram of gatifloxacin form W.

One characteristic of gatifloxacin form W is its powder x-ray diffraction diagram. Gatifloxacin form W can be characterized by x-ray reflections at about 7.8°, 10.8°, 13.7°, 18.6°, and 19.9°, ±0.2° 2θ. A typical x-ray diffraction diagram of gatifloxacin form W is shown in FIG. 5.

Figure 21:
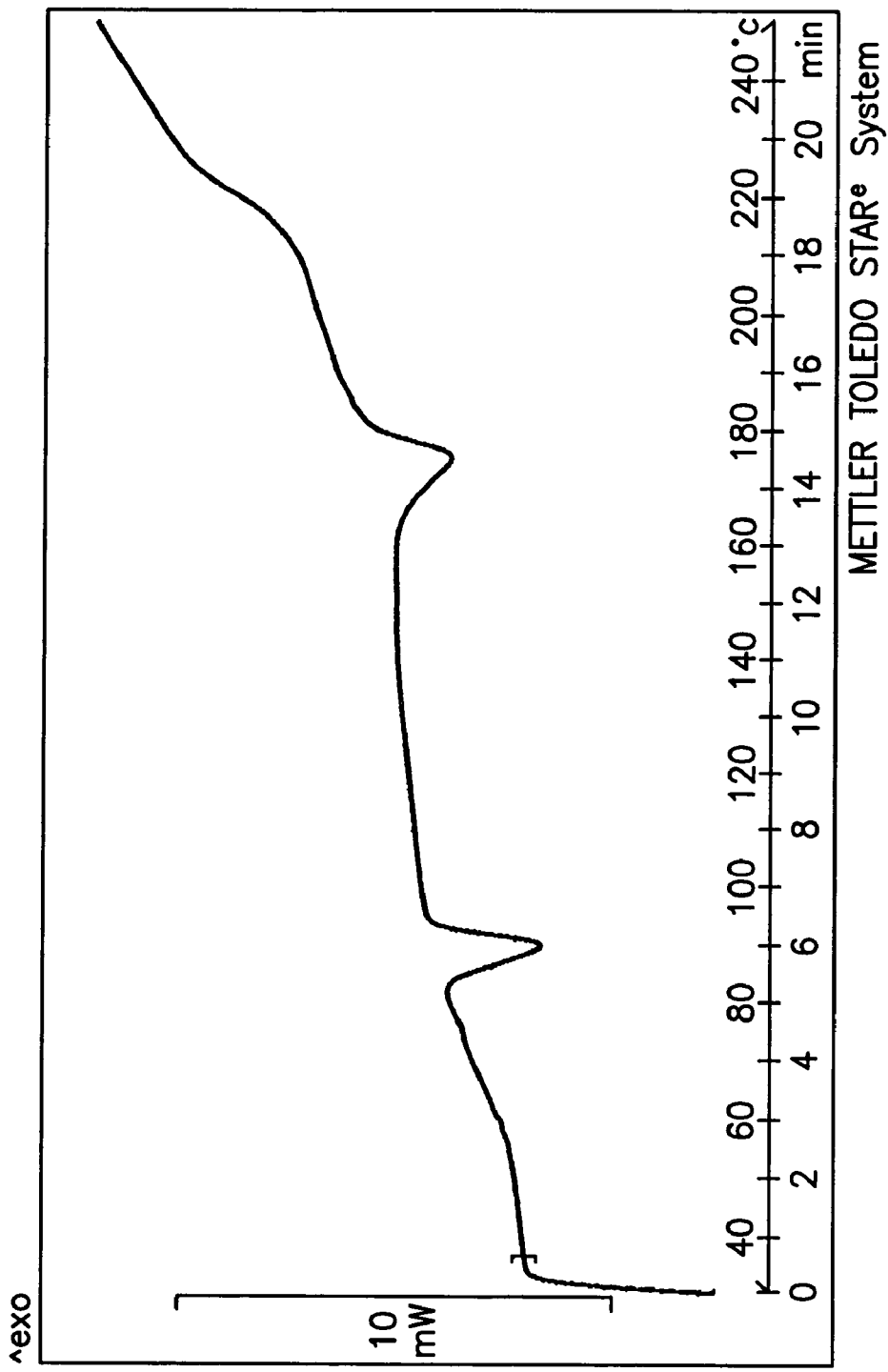
FIG. 21 is a representative DSC thermogram of gatifloxacin form W.

Another characteristic of gatifloxacin form W is the endotherms observed in its DSC thermogram. A typical DSC thermogram of gatifloxacin form W is shown in FIG. 21. The DSC thermogram of form W is characterized by an endotherm peak at about 90° C. and an additional endotherm peak at about 175° C. Gatifloxacin form W has a loss-on-drying (LOD) of between about 1 wt-% and about 3 wt-% in the temperature range of up to about 100° C.

The present invention also provides a method of making form W including the steps of: providing, at reflux temperature, a solution of gatifloxacin in acetonitrile having a concentration of about 0.3 M, combining, at reflux temperature, the solution with about one-tenth of its volume of polyethylene glycol, cooling the resulting solution to about 57° C. and seeding the solution with <<(gatifloxacin hemihydrate>>, maintaining the seeded solution at about 57° C. for about 2 hours, cooling the resulting seeded solution to about 5° C. at about 5° per hour, maintaining the resulting suspension at about 5° C. for a holding time, preferably about 12 hours, and isolating the crystalline form of gatifloxacin having at least one aforesaid characteristic of form W from the suspension.

In a preferred embodiment embodiment, the present invention provides a method of obtaining gatifloxacin form W comprising the steps of synthesizing gatifloxacin by forming a slurry of gatifloxacin and acetonitrile (10% w/v); heating to reflux, preferably at a temperature of about 80° C.; optionally maintaining the resulting mixture at a temperature of about 80° C. for a holding time; removing any undissolved matter from the solution by filtration; refluxing, preferably at a temperature of about 80° C.; adding polyethylene glycol (10% v/v); cooling the clear reaction mixture to a temperature of between about 56° C. and about 58° C.; recrystallizing by adding about 0.1 g gatifloxacin hemihydrate; optionally maintaining the resulting mixture at a temperature of between about 56° C. and about 58° C. for a holding time; cooling to a temperature of about 5° C., preferably at a cooling rate of between about 6.3° C. and 6.7° C. per hour; optionally maintaining the resulting mixture at a temperature of about 5° C. for a holding time; recovering gatifloxacin form W from the slurry by vacuum filtration; washing with acetonitrile; and drying recovered gatifloxacin form W at about 50° C., preferably under vacuum.

In yet another embodiment, the present invention provides a novel crystalline form of gatifloxacin, denominated form X, and methods for making it.

Figure 6:
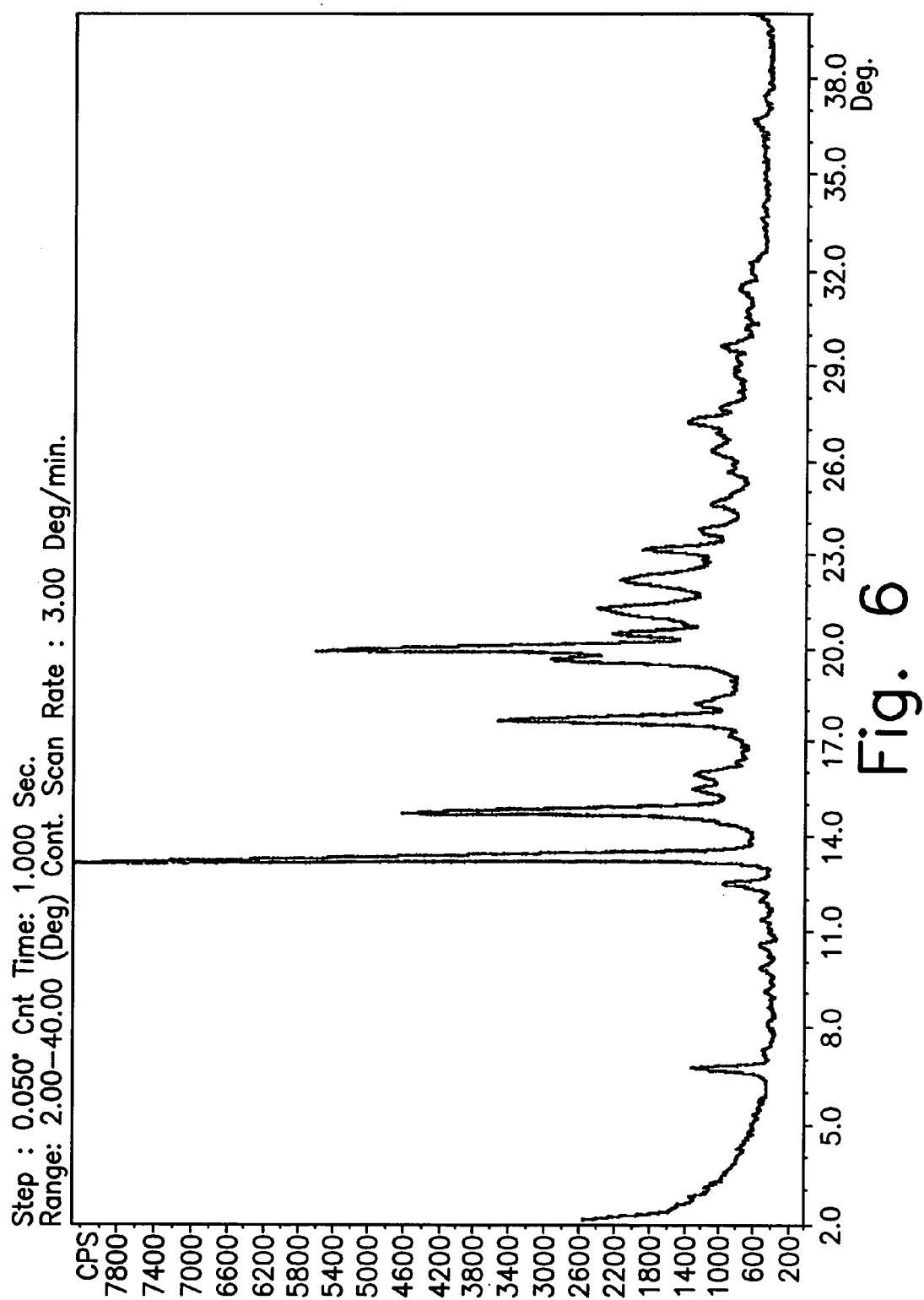
FIG. 6 is a representative x-ray diffraction diagram of gatifloxacin form X.

One characteristic of gatifloxacin form X is its powder x-ray diffraction pattern. Gatifloxacin form X is characterized by x-ray reflections at about 13.4°, 14.8°, 17.6°, 19.6°, and 20.0°, ±0.2° 2θ. A typical x-ray diffraction diagram for gatifloxacin form X is shown in FIG. 6.

Figure 22:
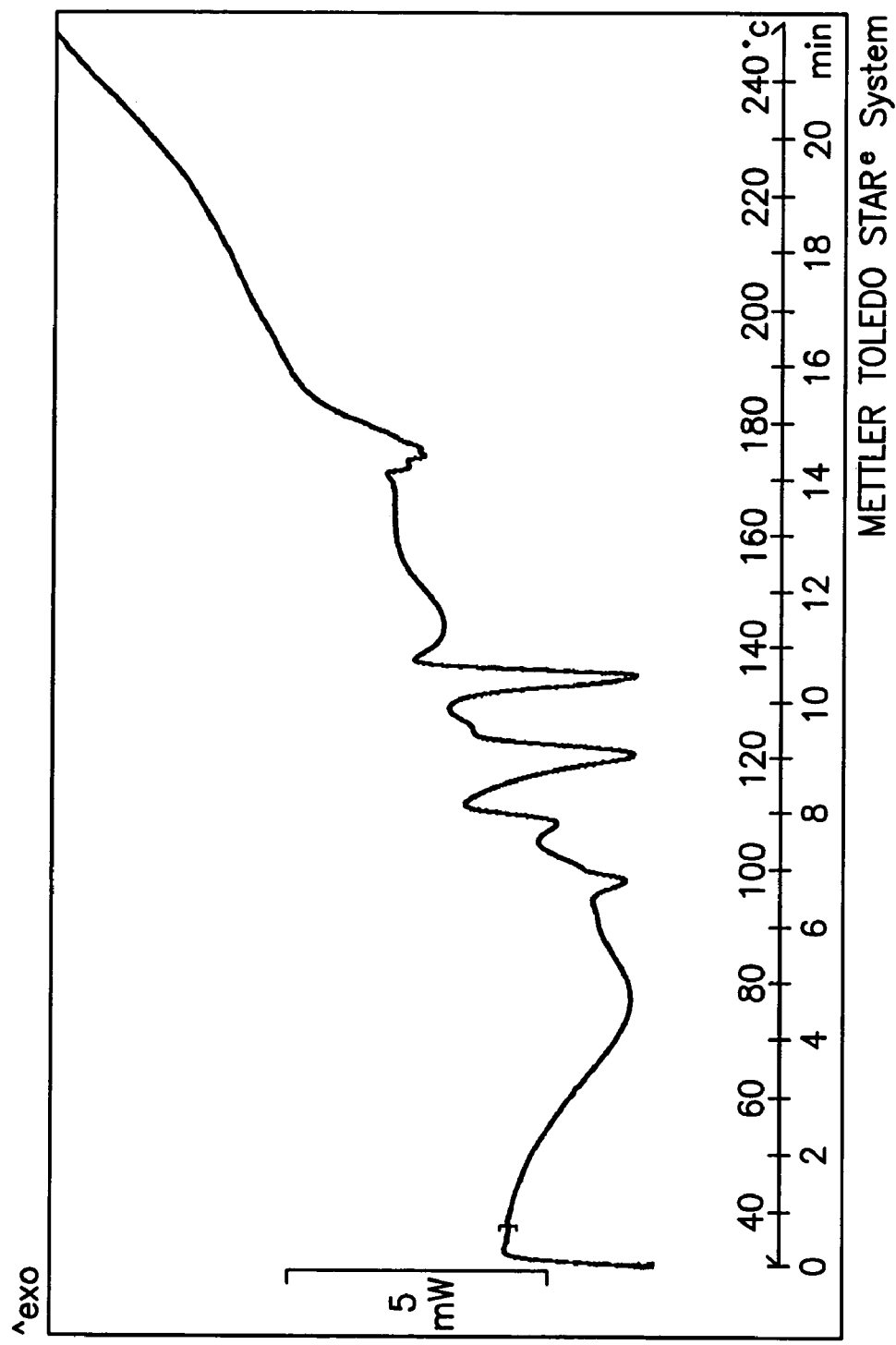
FIG. 22 is a representative DSC thermogram of gatifloxacin form X.

Another characteristic of gatifloxacin form X is the endothermic peak observed in the DSC thermogram of the material. A typical DSC thermogram of gatifloxacin form X is shown in FIG. 22. The DSC thermogram of gatifloxacin form X is characterized by endotherms peaking at about 99° C., 122° C., 135° C. and 140° C.

Thermogravimetric analysis of gatifloxacin form X shows a loss-on-drying (LOD) of between about 20 wt-% and about 28 wt-% in the temperature range of between about 25° C. and about 200° C.

In another and preferred embodiment, the present invention relates to a method of obtaining gatifloxacin form X comprising the steps of synthesizing gatifloxacin from 2-methylpiperazine and 1-cyclopropyl-6,7-difluoro-1,4-dihydro-8-methoxy-4-oxo-3-quinolinecarboxylic acid in solution in DMSO by heating to about 55° C., optionally maintaining the resulting mixture at a temperature of about 55° C. for a holding time; diluting the reaction mixture with ⅓ total starting volume of 2.5 parts toluene: 1 part water preheated to about 55° C.; cooling the diluted reaction mixture to a temperature of about 5° C., preferably at a cooling rate of between about 12° C. and about 13° C. per hour; optionally maintaining the resulting mixture at a temperature of about 5° C. for a holding time; heating the reaction mixture to a temperature of about 35° C., preferably at a heating rate of about 30° C. per hour; optionally maintaining the resulting mixture at a temperature of about 35° C. for a holding time; repeating once additionally the cycle of cooling the diluted reaction mixture to a temperature of about 5° C., and heating to a temperature of about 35° C., preferably at a cooling rate of between about 7° C. and about 8° C. per hour and a heating rate of about 30° C. per hour, optionally maintaining the resulting mixture at the respective temperatures of about 5° C. and about 35° C. for a holding time; cooling the diluted reaction mixture to a temperature of about 10° C., preferably at a cooling rate between about 4.0° C. and 4.2° C. per hour; optionally maintaining the resulting mixture at a temperature of about 10° C. for a holding time; and recovering gatifloxacin form X by vacuum filtration from the resulting suspension and washing with acetonitrile.

In still yet a further embodiment, the present invention provides a novel crystalline form of gatifloxacin, denominated form Y, and methods for making it.

Figure 7:
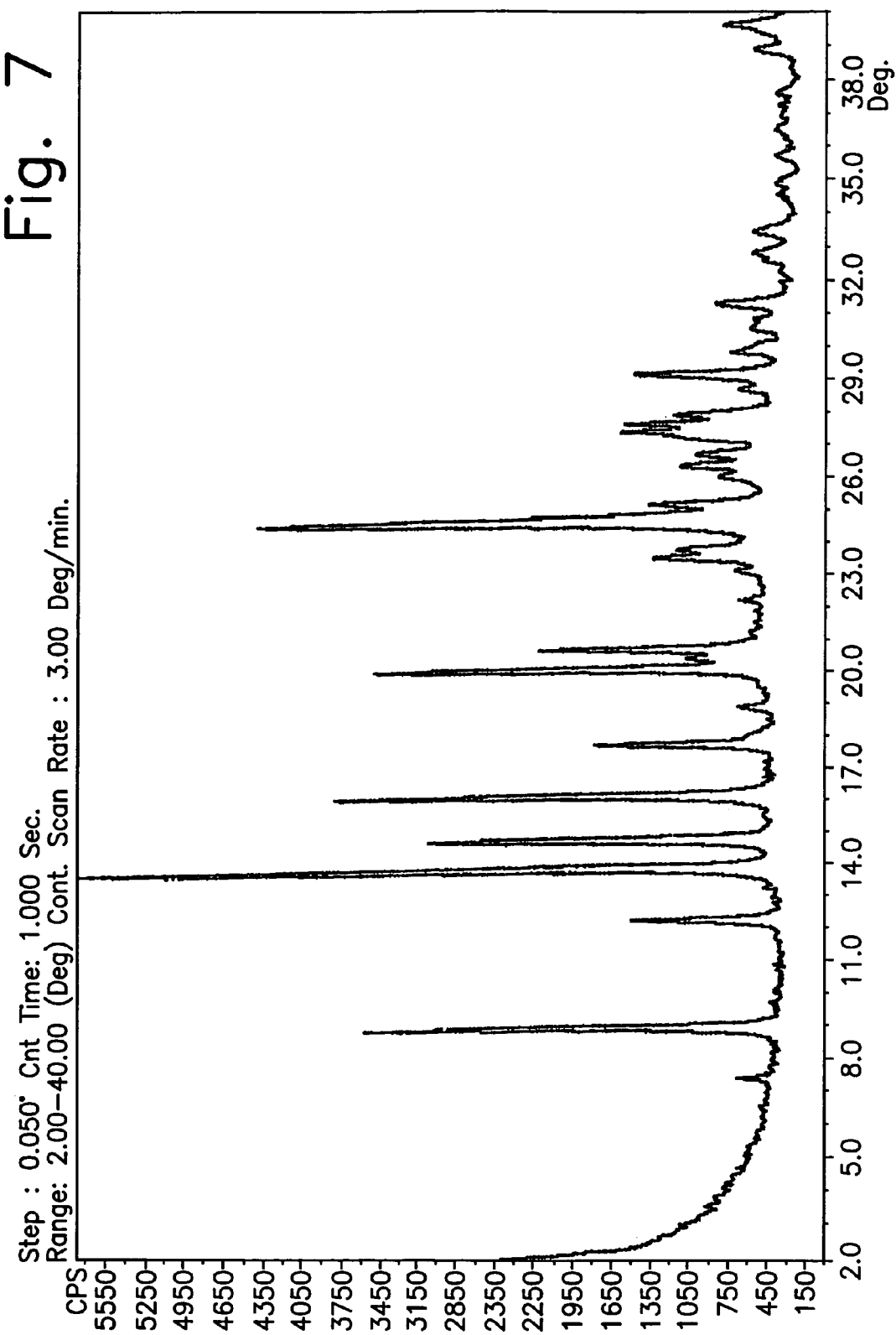
FIG. 7 is a representative x-ray diffraction diagram of gatifloxacin form Y.
Figure 8:
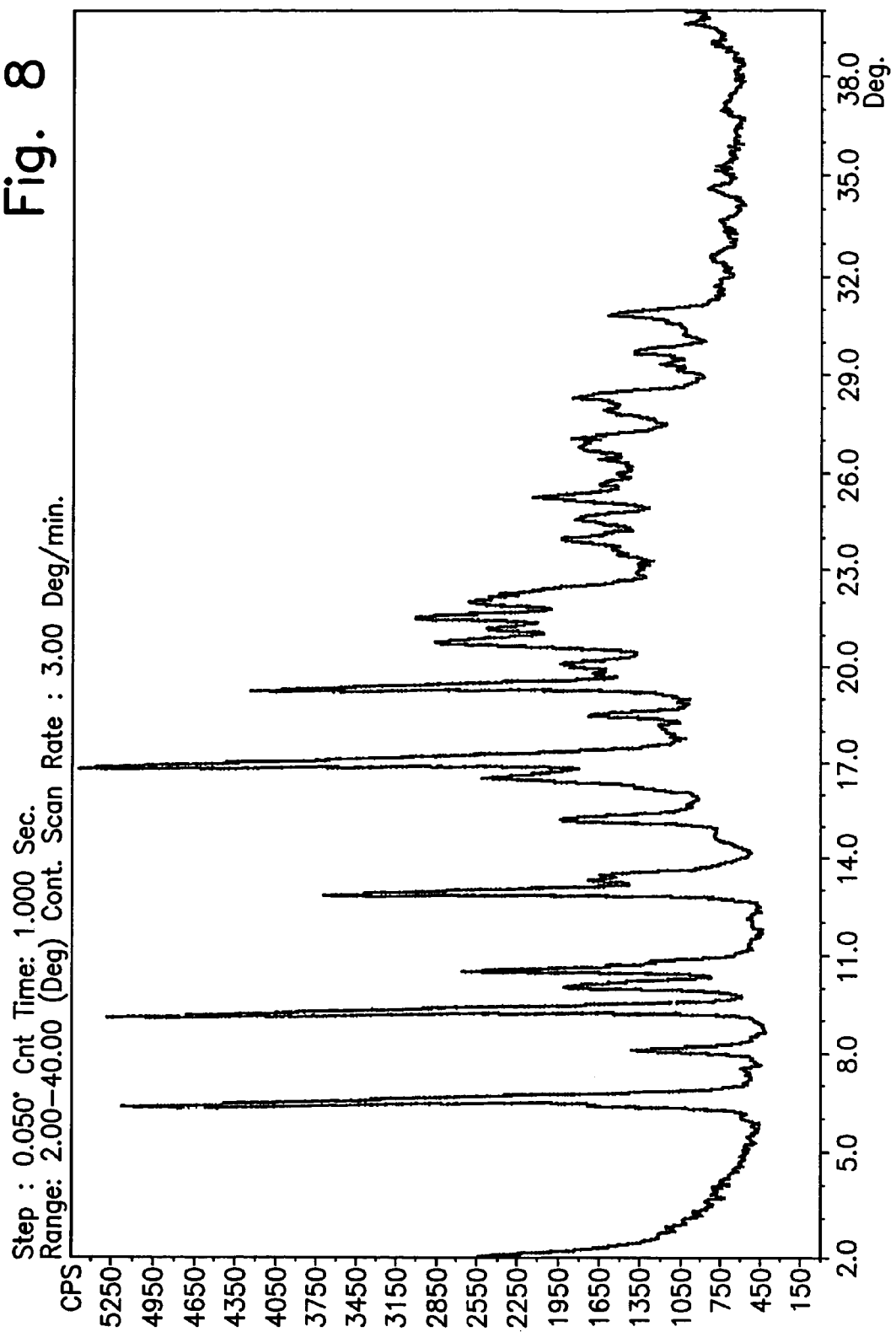
FIG. 8 is a representative x-ray diffraction diagram of gatifloxacin form Z.

Gatifloxacin form Y can be characterized by x-ray reflections at about 13.9°, 14.8°, and 16.1°, ±0.2° 2θ. A typical x-ray diffraction diagram of form Y, obtained on "as is" sample is shown in FIG. 7.

Figure 23:
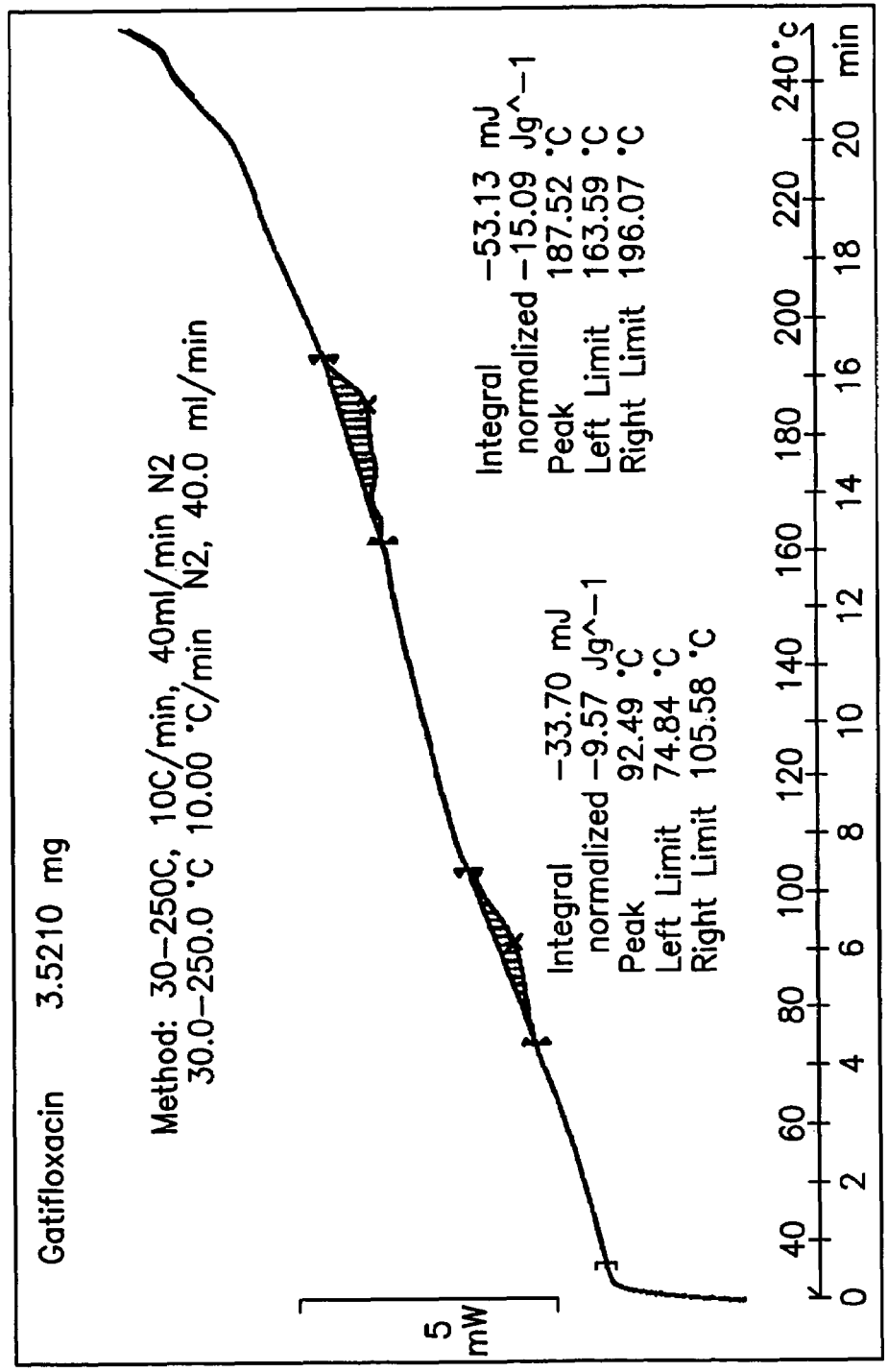
FIG. 23 is a representative DSC thermogram of gatifloxacin form Y.

Another characteristic of gatifloxacin form Y is the endothermic peaks observed in the DSC thermogram of form Y. Form Y has characteristic endotherms that peak at about 92° and about 188° C. A typical DSC thermogram of gatifloxacin form Y is shown in FIG. 23.

Figure 24:
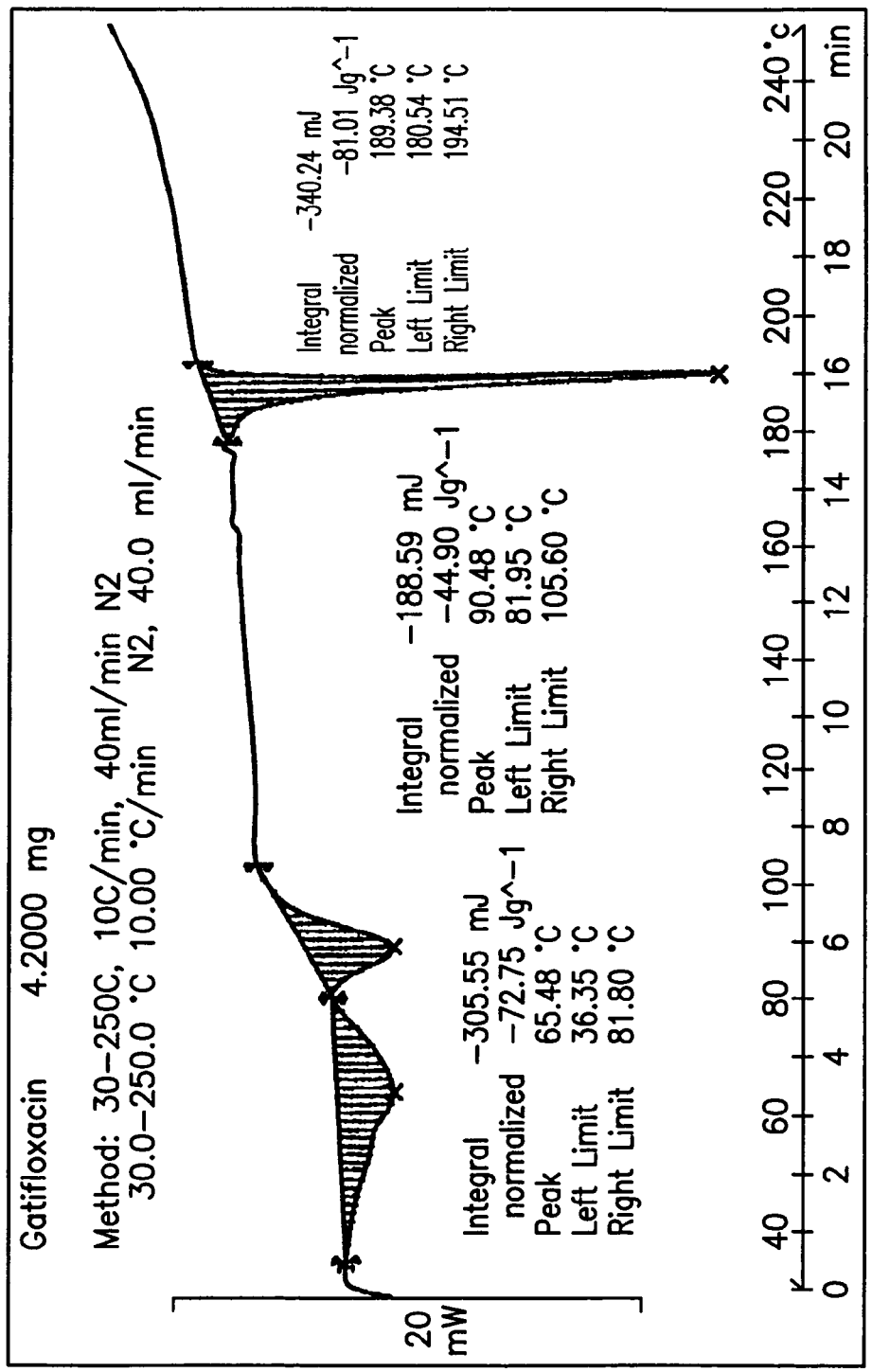
FIG. 24 is a representative DSC thermogram of gatifloxacin form Z.
Figure 25:
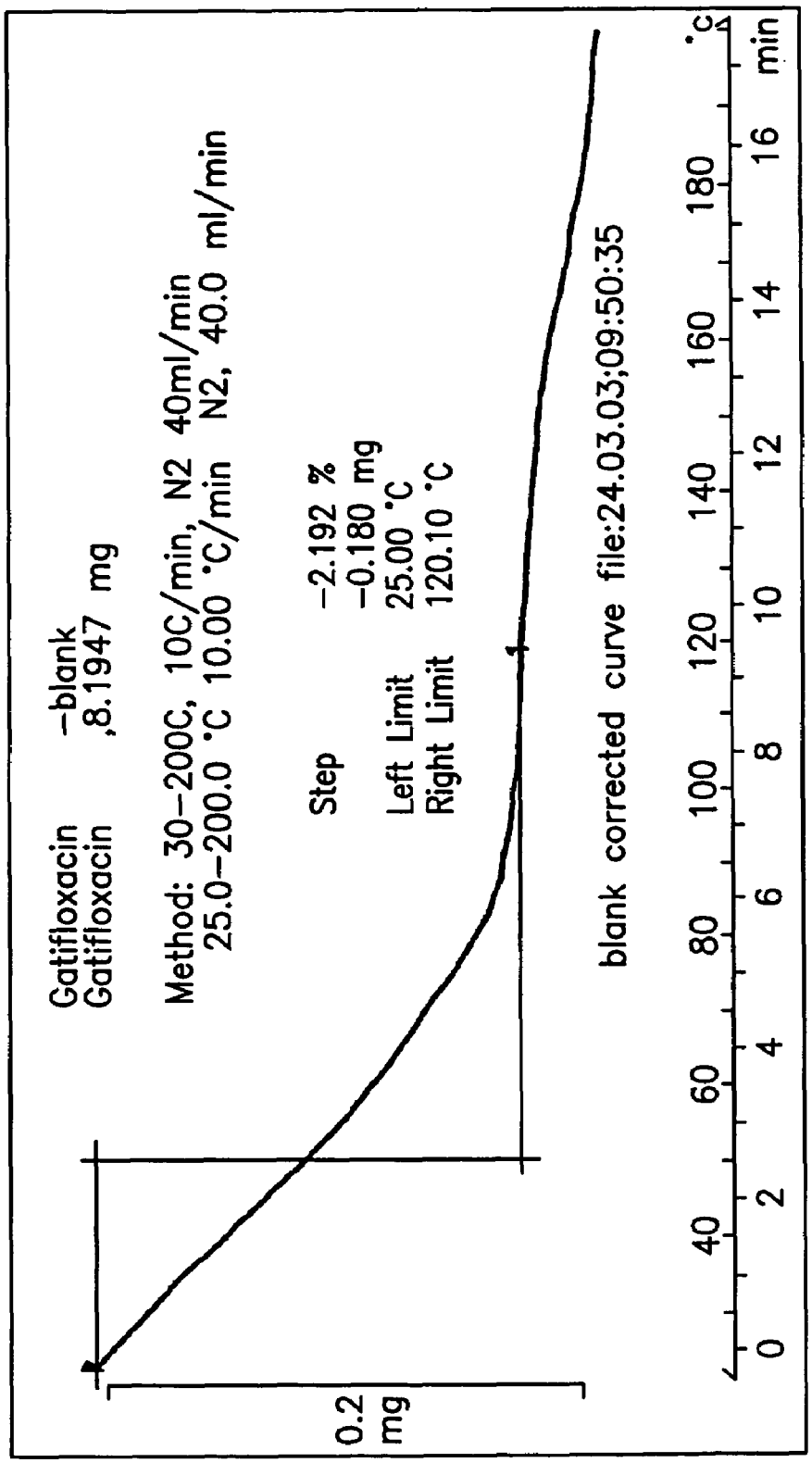
FIG. 25 is a representative TGA thermogram of gatifloxacin form Y.

Gatifloxacin form Y has a loss-on-drying (LOD) of about 2 wt-% to about 3 wt-% in the temperature range of up to about 120° C. A typical TGA thermogram of form Y is shown in FIG. 24. The water content of gatifloxacin form Y is about 2% to about 3%, as determined by Karl Fisher (KF) analysis.

Gatifloxacin form Y can be made by providing a slurry of gatifloxacin-HCl in acetonitrile:water (90:10, v:v, ca. 16.7% w/v) at about 5° C.; combining the suspension with a volume of aqueous NaOH (e.g. 47%) sufficient to neutralize at least about 70 mole % of the hydrochloride (i.e. convert it to the free base); and isolating solid gatifloxacin from the resulting suspension. The isolated (recovered) gatifloxacin is washed with acetonitrile:water (90:10) and dried at a temperature of about 50° C. at reduced pressure.

In another embodiment, the present invention provides a novel crystalline form of gatifloxacin, denominated form Z, and methods for making it.

One characteristic of gatifloxacin form Z is the reflections observed in powder x-ray diffraction. Gatifloxacin form Z can be characterized by x-ray reflections at about 6.7°, 9.5°, 10.7°, 13.1°, and 17.2°, ±0.2° 2θ. A typical x-ray diffraction diagram of gatifloxacin form Z is shown in FIG. 23.

Another characteristic of gatifloxacin form Z is the series of endotherms observed in DSC thermograms of form Z. A typical DSC thermogram of gatifloxacin form Z is shown in FIG. 24. The DSC thermogram of form Z is characterized by a broad endotherm peak at about 65° C., an additional broad endotherm peak at about 90° C., and a sharp endotherm peak at about 190° C.

Figure 26:
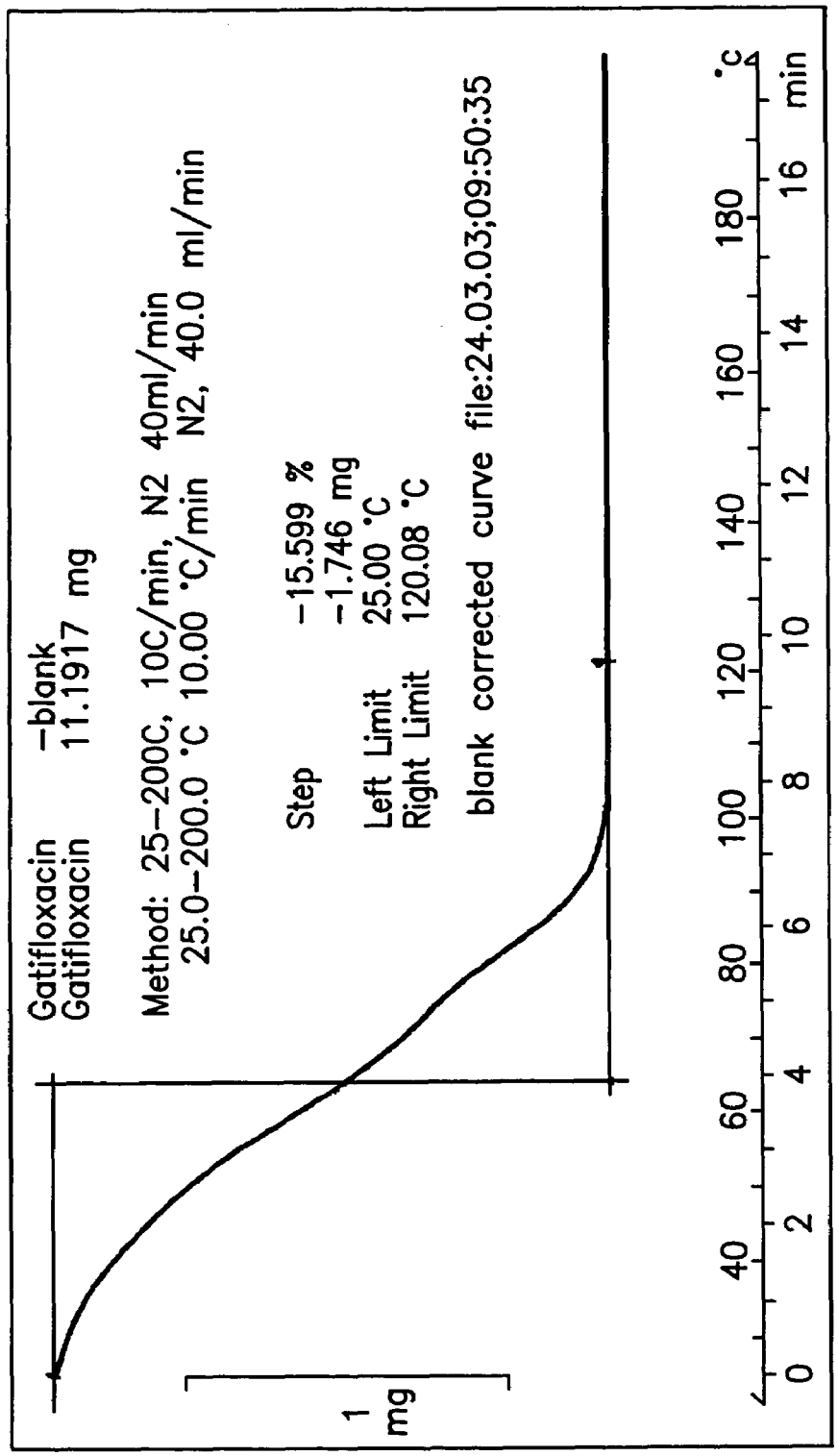
FIG. 26 is a representative TGA thermogram of gatifloxacin form Z.

Gatifloxacin form Z has an LOD of between about 14 wt-% and about 18 wt-% in the temperature range of up to about 120° C. A typical TGA thermogram for gatifloxacin form Z is shown in FIG. 26. Water content of gatifloxacin form Z is about 8% to about 10%, as determined by KF analysis. Gatifloxacin form Z also contains acetonitrile.

Gatifloxacin form Z can be made by providing a suspension of gatifloxacin in acetonitrile, about 11% (w/v), heating the suspension to reflux, preferably at a temperature of about 80° C.; optionally maintaining the resulting mixture at a temperature of about 80° C. for a holding time; removing any undissolved matter from the solution by filtration whereby a hot-filtered solution of gatifloxacin is obtained; cooling the clear reaction mixture to a temperature of about 60° C., preferably at a cooling rate of between about 0.6° C. and 0.7° C. per minute; optionally maintaining the resulting mixture at a temperature of about 60° C. for a holding time; cooling the reaction mixture further to a temperature of about 5° C., preferably at a cooling rate of between about 20° C. and 24° C. per hour without seeding; optionally maintaining the resulting mixture at a temperature of about 5° C. for a holding time; recovering gatifloxacin form Z from the suspension. Gatifloxacin form Z so formed contains about 8% to about 10% water and also contains acetonitrile.

In yet another embodiment, the present invention provides a novel crystalline form of gatifloxacin, denominated form CH1, and methods for making it.

Figure 9:
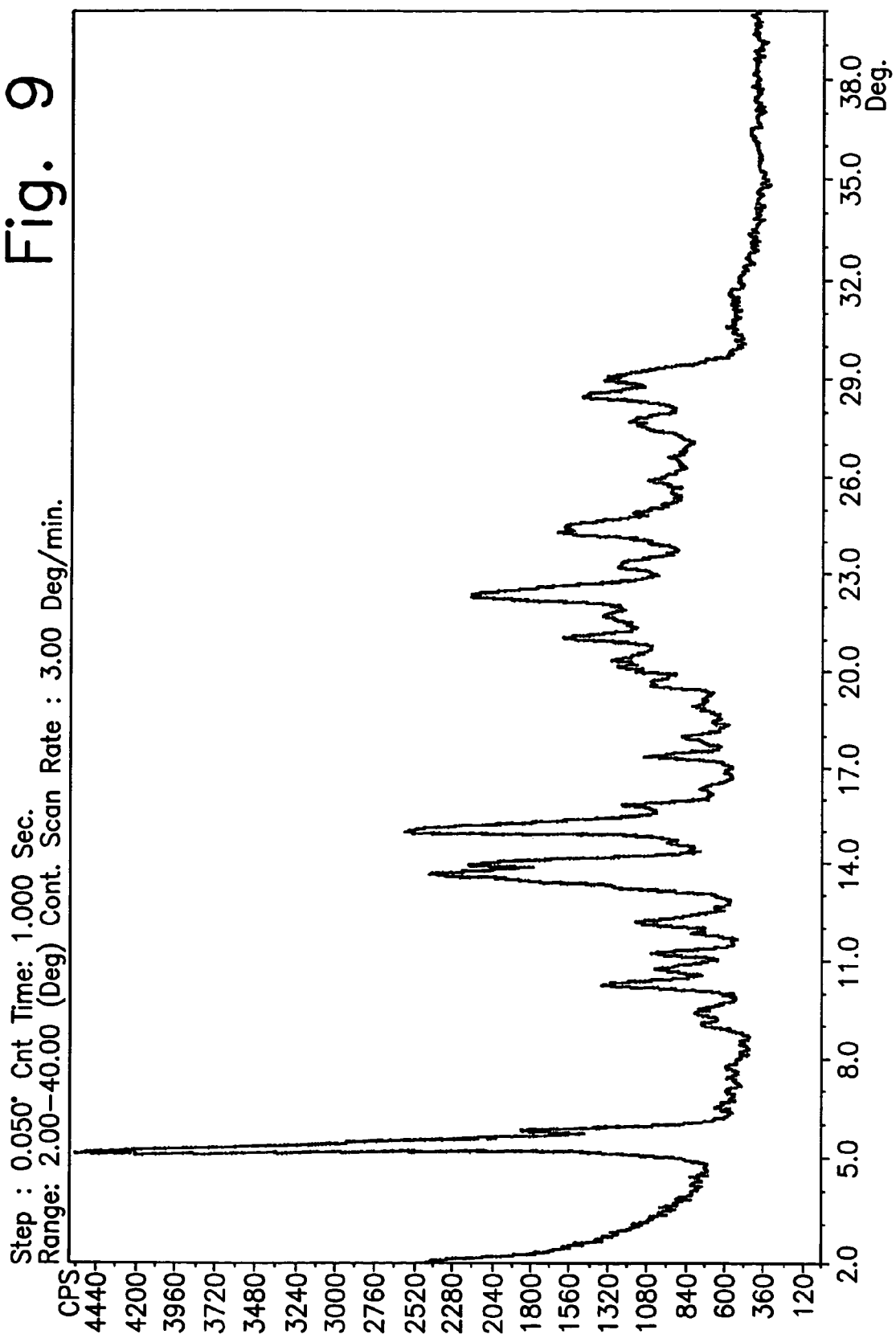
FIG. 9 is a representative x-ray diffraction diagram of gatifloxacin form CH1.

One characteristic of gatifloxacin form CH1 is its powder x-ray diffraction pattern. Gatifloxacin form CH1 is characterized by x-ray reflections at about 5.5°, 10.3°, 10.8°, 13.9°, and 15.1°, ±0.2° 2θ. A typical x-ray diffraction diagram for gatifloxacin form CH1 is shown in FIG. 9.

Gatifloxacin form CH1 can be made by heating form CY at about 90° C. and about 150° C., preferably about 100° C., for at least about 30 minutes.

In yet another embodiment, the present invention provides a novel crystalline form of gatifloxacin, denominated form CH2, and methods for making it.

Figure 10:
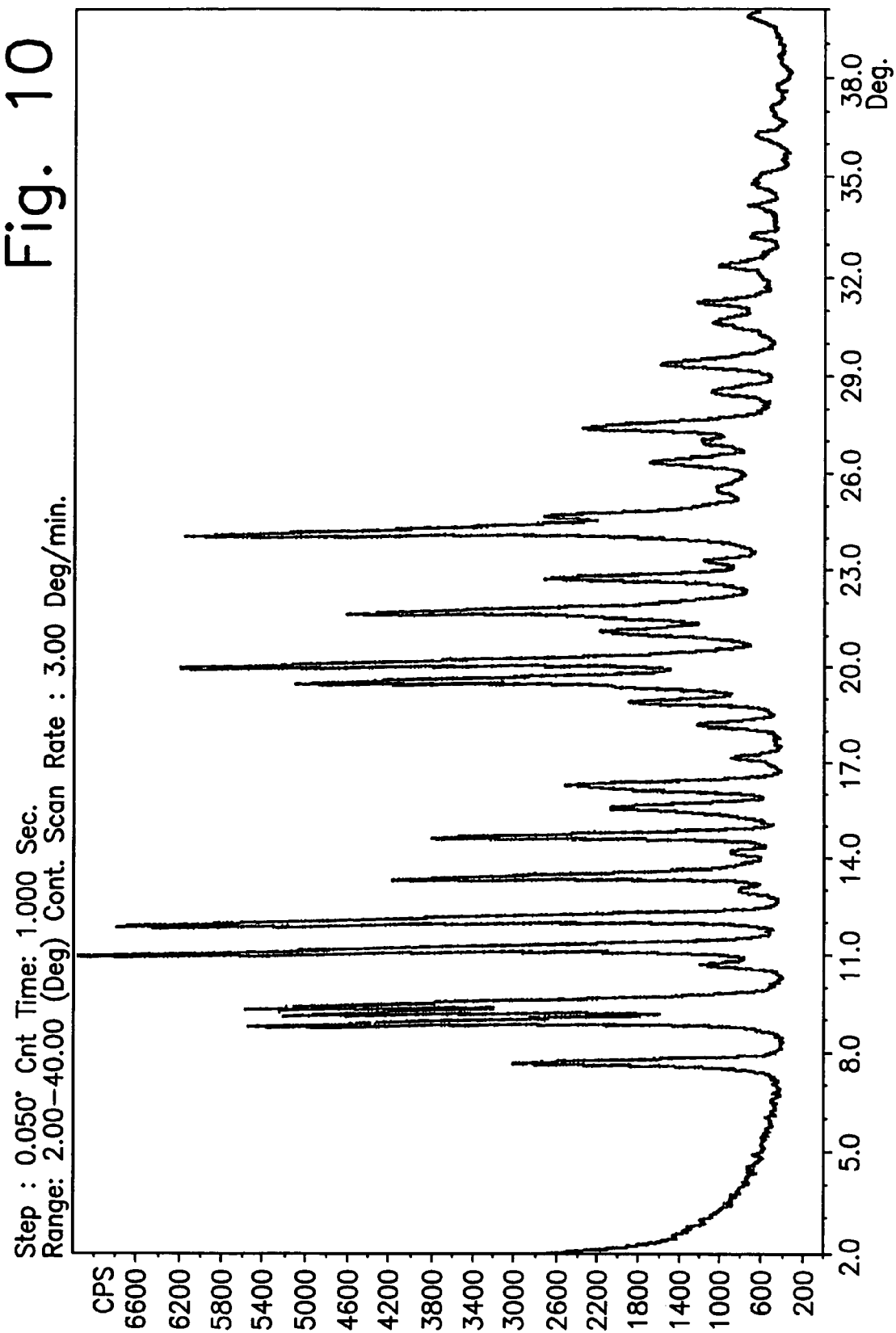
FIG. 10 is a representative x-ray diffraction diagram of gatifloxacin form CH2.

One characteristic of gatifloxacin form CH2 is its powder x-ray diffraction pattern. Gatifloxacin form CH2 is characterized by x-ray reflections at about 7.8°, 9.1°, 9.4°, and 9.6°, ±0.2° 2θ. A typical x-ray diffraction diagram for gatifloxacin form CH2 is shown in FIG. 10.

Gatifloxacin form CH2 can be made by heating form V, discussed hereinbelow, at about 50° C. to about 80° C., preferably for about 15 minutes. Gatifloxacin so formed is a mixture of form V and form CH2. Gatifloxacin form V is a crystalline form of gatifloxacin, characterized by x-ray reflections (peaks) at about 6.0°, 14.1°, 21.1°, and 22.5°, ±0.2° 2θ.

Form CH2 can also be made by heating the pentahydrate form of gatifloxacin. (gatifloxacin pentahydrate) at about 70° C. to about 120° C. for a holding time, preferably for about 30 minutes.

Gatifloxacin form CH2 can also be made by heating form CW to between about 70° C. and about 120° C. for a holding time, preferably for about 30 minutes. Gatifloxacin form CW is a crystalline form of gatifloxacin.

Gatifloxacin form CH2 can also be made by heating form Ω to between about 25° C. and about 50° C. at a relative humidity of about 60% to about 80%, preferably for at least about one month. Gatifloxacin so formed is a mixture of form Ω and form CH2.

A further embodiment of the present invention provides a novel crystalline form of gatifloxacin, denominated form RH, and methods for making it.

Figure 11:
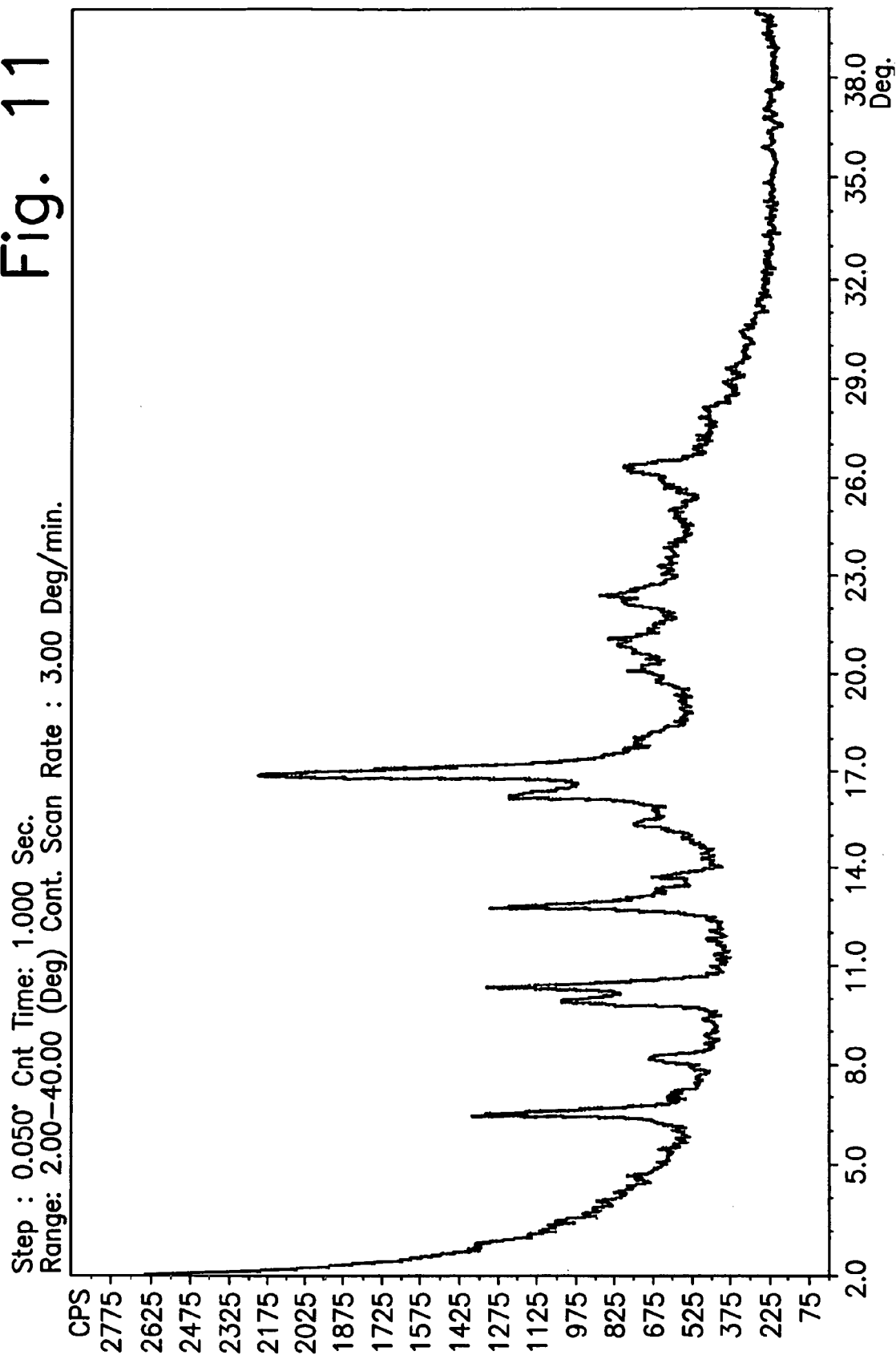
FIG. 11 is a representative x-ray diffraction diagram of gatifloxacin form RH.

One characteristic of gatifloxacin form RH is its powder x-ray diffraction pattern. Gatifloxacin form RH is characterized by x-ray reflections at about 6.6°, 9.9°, 10.5°, and 12.9°, ±0.2° 2θ. A typical x-ray diffraction diagram for gatifloxacin form RH is shown in FIG. 11.

Gatifloxacin form RH can be made by heating form R at about 50° C. to about 70° C., preferably for about 30 minutes. Gatifloxacin form R is a crystalline form of gatifloxacin, characterized by an XRD pattern with peaks at about 6.7°, 13.2°, and 15.2°, ±0.2° 2θ. Gatifloxacin form R may be prepared through a solution of gatifloxacin in acetonitrile. Gatifloxacin is added to acetonitrile and the mixture is heated if necessary to obtain a solution. The solution is the cooled to from about 0° C. to about 10° C., more preferably about 5° C. Gatifloxacin then crystallizes out of the solution and is separated by conventional techniques, preferably filtration under vacuum and washed with an excess amount of acetonitrile if necessary to obtain a complete transformation.

In yet another embodiment, the present invention provides a novel crystalline form of gatifloxacin, denominated form HX1.

Figure 12:
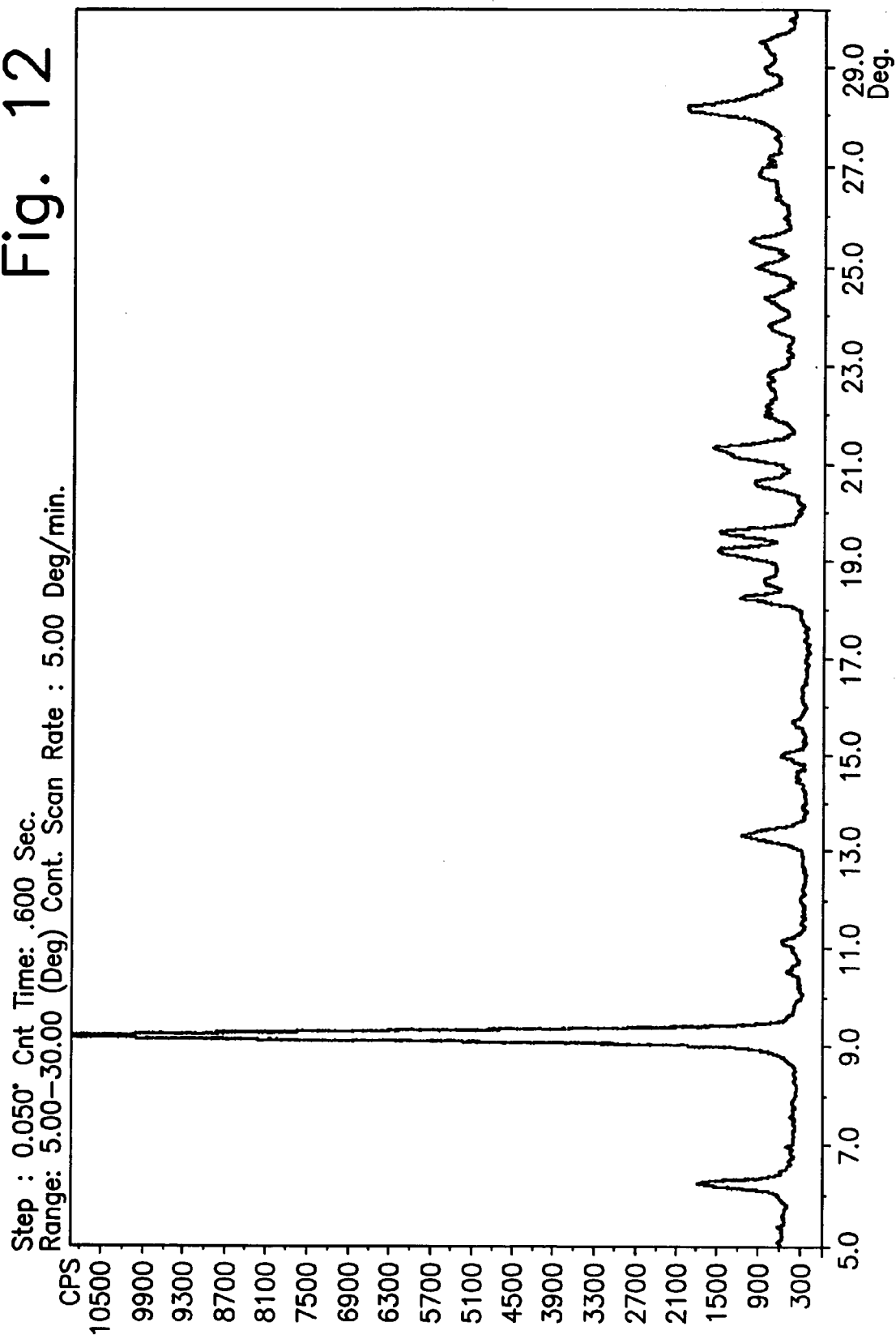
FIG. 12 is a representative x-ray diffraction diagram of gatifloxacin form HX1.

Gatifloxacin form HX1 is characterized by x-ray reflections at about 6.3°, 9.3°, 19.3°, 20.8°, 24.5°, and 25.1°, ±0.2° 2θ. A typical x-ray diffraction diagram for gatifloxacin form HX1 is shown in FIG. 12.

Gatifloxacin form HX1 can be made by forming a slurry of DMSO-wet gatifloxacin and water (20% w/v); stirring the resulting mixture at ambient temperature, preferably between about 30 minutes and not more than about 90 minutes; recovering gatifloxacin form HX1 from the suspension, for example, by filtration. Gatifloxacin form HX1 so formed contains between about 30% and about 50% water content by KF analysis.

DMSO-wet gatifloxacin refers to gatifloxacin that has been isolated from a suspension or slurry of gatifloxacin in DMSO, preferably a slurry or suspension obtained by crystallization of gatifloxacin from its solution in DMSO.

In yet another embodiment, the present invention provides a novel crystalline form of gatifloxacin, denominated form HX2, and methods for making it.

Figure 13:
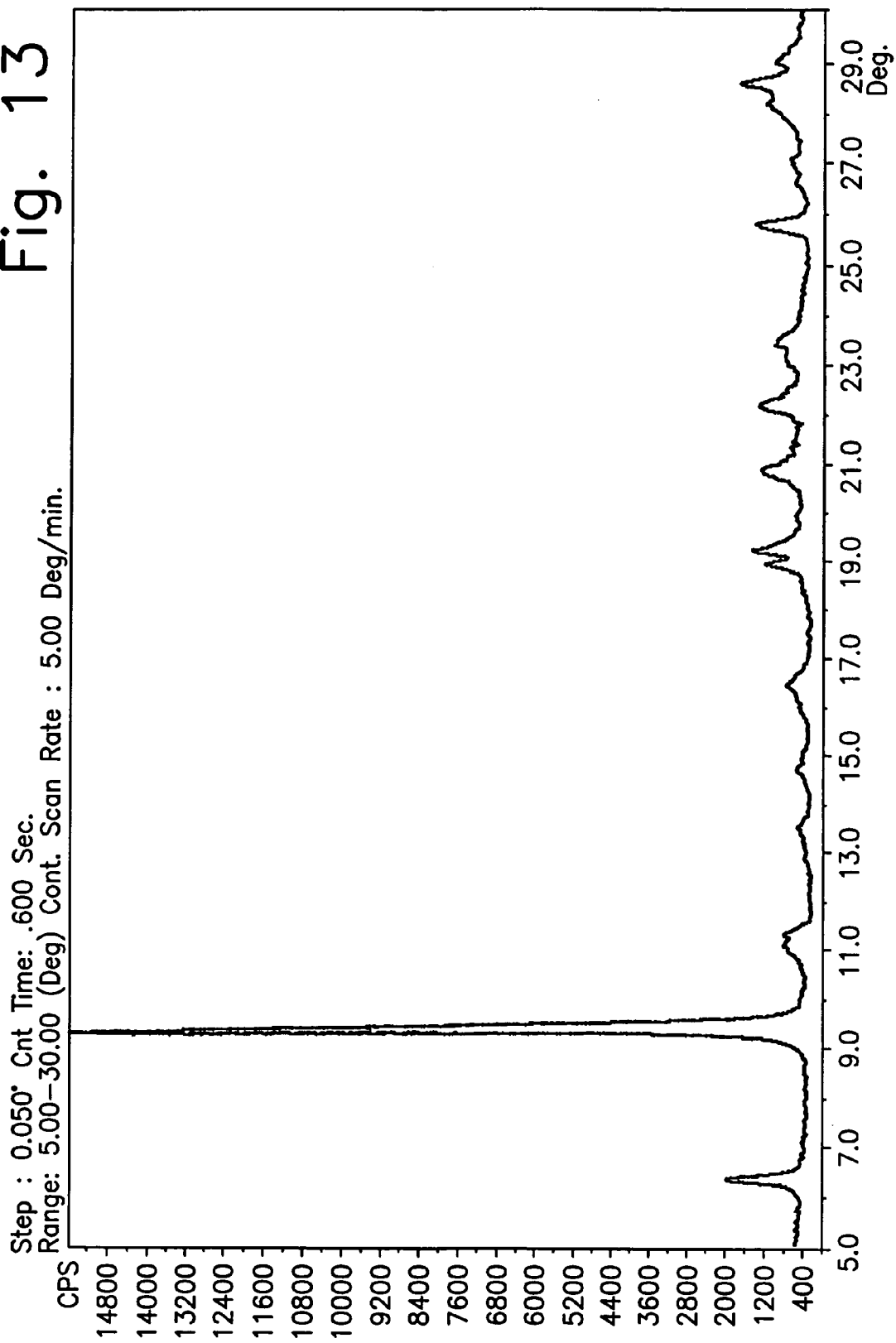
FIG. 13 is a representative x-ray diffraction diagram of gatifloxacin form HX2.

Gatifloxacin form HX2 is characterized by reflections in XRD analysis at about 6.4°, 9.4°, 16.4°, 18.9°, and 19.2°, ±0.2° 2θ. A typical x-ray diffraction diagram for gatifloxacin form HX2 is shown in FIG. 13.

Gatifloxacin form HX2 can be made by forming a slurry of DMSO-wet gatifloxacin and water (20% w/v); stirring the resulting mixture at ambient temperature, preferably between at least about 90 minutes and about 180 minutes, especially about 180 minutes; recovering gatifloxacin form HX2 from the suspension, for example, by filtration. Gatifloxacin form HX2 so formed contains between about 30% and about 50% water content by KF analysis.

In yet a further embodiment, the present invention provides novel methods for making gatifloxacin form T2RP. As used herein, gatifloxacin form T2RP refers to the form disclosed under such name in U.S. Pat. No. 6,413,969 (WO 02/22126). Gatifloxacin form T2RP can be made by heating gatifloxacin form CW between about 135° C. and about 150° C., preferably for about 30 minutes. Gatifloxacin form CW can be obtained, for example, by drying gatifloxacin form CX under vacuum at about 50° C., as described above.

Other conditions under which gatifloxacin forms Y, Z, CH1, CH2, RH, V, T2RP, HX1 or HX2 are formed may be empirically determined.

In another embodiment, any of the novel crystlline forms of gatifloxacin polymorphs or pseudopolymorphs described herein, alone or in any combination, are formulated into a pharmaceutical composition, preferably an oral solid dosage form or a dosage form for parental administration. Such compositions include at least one crystalline form of gatifloxacin that has at lest one characteristic of at least one of forms CW, CX, CY, CZ, W, X, Y, Z, CH1, CH2, RH, HX1, or HX2.

The pharmaceutical composition can be in the form of a solid oral dosage form (e.g., compressed tablets or capsules), or it can be in the form of a liquid oral dosage form (e.g., a solution or oral suspension).

Compressed tablets can be made by dry or wet granulation methods as is known in the art. In addition to the pharmaceutically active agent or drug, compressed tablets contain a number of pharmacologically inert ingredients, referred to as excipients. Some excipients allow or facilitate the processing of the drug into tablet dosage forms. Other excipients contribute to proper delivery of the drug by, for example, facilitating disintegration.

Excipients can be broadly classified according to their intended function. However, it must be kept in mind that a particular excipient can function in more than one way.

Diluents increase the bulk of a solid pharmaceutical composition and may make a pharmaceutical dosage form containing the composition easier for the patient and caregiver to handle. Diluents for solid compositions include, for example, microcrystalline cellulose (e.g., AVICEL®, microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form like a tablet may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium aiginate and starch. The dissolution rate of a compacted solid pharmaceutical composition in the patient's stomach may be increased by the addition of a disintegrant to the composition.

Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flow properties of non-compacted solid compositions and improve the accuracy of dosing. Excipients that may function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid ethyl maltol, and tartaric acid.

Solid and liquid compositions may also be colored using any pharmaceutically acceptable colorant to improve their appearance and/or facilitate patient identification of the product and unit dosage level.

Of course, wet or dry granulate can also be used to fill capsules, for example gelatin capsules. The excipients chosen for granulation when a capsule is the intended dosage form may or may not be the same as those used when a compressed tablet dosage form is contemplated.

Selection of excipients and the amounts to use may be readily determined by the formulation scientist based upon experience and consideration of standard procedures and reference works in the field.

In liquid pharmaceutical compositions of the present invention, one of gatifloxacin forms CW, CX, CY, CZ, W, X, Y, Z, CH1, CH2, RH, HX1, HX2, or mixtures thereof, and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include for example acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as gluconic acid, lactic acid, citric acid or acetic acid, sodium gluconate, sodium lactate, sodium citrate or sodium acetate.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. The most suitable route in any given case will depend on the nature and severity of the condition being treated. The dosages can be conveniently presented in unit dosage form and prepared by any of the methods well-known in the pharmaceutical arts.

Dosage forms include solid dosage forms like tablets, powders, capsules, suppositories, sachets, troches and lozenges as well as liquid syrups, suspensions and elixirs.

The active ingredient and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms may be administered in various dosages depending on the need.

The present invention can be further illustrated with the following non-limiting examples.

EXAMPLES

Example 1

Preparation of CW and CX

A 10 liter reactor equipped with mechanical stirrer, condenser and thermometer, was charged with 1-cyclopropyl-6,7-difluoro-1.4-dihydro-8-methoxy-4-oxo-3-quinolinecarboxylic acid (450 g), DMSO (9 L), and 2-methylpiperazine (320.5 g). The reaction mixture was then heated to 55° C. and stirred at a rate of 250 rpm under nitrogen atmosphere. The temperature was maintained for 24 hours until completion of the reaction. Water (1.8 L) was added at this temperature.

The mixture was cooled to 0° C. during 5 hours and maintained with stirring for 12 hours at this temperature. The suspension was filtered under vacuum and washed with acetonitrile (675 ml) to obtain 668 g of wet material.

X-ray diffraction analysis of the wet sample showed it to be form CX.

The wet solid form CX was dried in a vacuum oven (reduced pressure) at 50° C. for 8 hours. X-ray analysis of the dried material showed it to be form CW.

Example 2

Preparation of Form CY

A 1 liter reactor equipped with mechanical stirrer, condenser and thermometer, was charged with 1-cyclopropyl-6,7-difluoro-1.4-dihydro-8-methoxy-4-oxo-3-quinolinecarboxylic acid (40 g), DMSO (800 mL) and 2-methylpiperazine (30.5 g). The reaction mixture was then heated to 55° C. and stirred for 24 hours until completion of the reaction.

Most of the DMSO (600 mL) was distilled off under high vacuum (3 mm Hg) during 1.5 hour at 70° C. The mixture was then cooled to 40° C. and water (160 mL) was added at this temperature. The solution was cooled to 5° C. and maintained at this temperature for 20 hours.

The suspension was filtered under vacuum and washed with acetonitrile (180 ml). The solid was dried under vacuum at 50° C. for 2 hours and then was charged to a reactor with 100 mL of acetonitrile. After 5 minute of slurry, the mixture was filtered again under vacuum without washing.

The recovered solid was then dried overnight under vacuum at 50° C.

X-ray analysis showed the dried solid to be form CY.

Example 3

Preparation of GTF Form CZ

A 100-liter reactor equipped with mechanical stirrer, condenser and thermometer, was charged with 1-cyclopropyl-6,7-difluoro-1.4-dihydro-8-methoxy-4-oxo-3-quinolinecarboxylic acid (3 kg), dimethylsulfoxide (DMSO) (60 L) and 2-methylpiperazine (2.14 kg). The reaction mixture was then heated to 55° C. and stirred at a rate of 110 rpm under nitrogen atmosphere. The temperature was maintained for 24 hours until completion of the reaction. Toluene and $H_2O$ (2.5:1) were added in a total volume of 21 liters at 55° C.

The resulting mixture was cooled to 11° C. over 4 hours and maintained with stirring for 1 hour at this temperature. The mixture was heated to 35° C. over 1 hour and maintained with stirring for 1 hour at 35° C. The mixture was then cooled to 11° C. over 6 hours and maintained, with stirring, for 12 hours at 11° C. The suspension obtained was filtered (suction) and washed with acetonitrile (6 L). The yield of gatifloxacin form CZ was 4.5 kg of wet material.

Example 4

Preparation of GTF Form W

A 0.5-liter reactor equipped with mechanical stirrer, condenser and thermometer, was charged with GTF-crude dry (40 g) and acetonitrile (400 ml). The slurry was then heated to reflux (80° C.) and stirred at 400 rpm for 2 hours at 80° C. to effect dissolution. The solution was filtered. The solution was heated to reflux and polyethylene glycol (40 ml) was added. The clear solution obtained was cooled to between 56° C. and 58° C. and GTF hemihydrate (0.1 g) was added.

At the end of the addition, the stirring was maintained for 2 hours at between 56° C. and 58° C., then cooled to 5° C. over 8 hours and maintained with stirring for 2 hours at 5° C. The slurry was filtered under vacuum and the collected solids washed with acetonitrile (60 ml) to obtain 54.38 g of wet material.

X-ray analysis showed the wet material to be GTF form W.

A portion of the wet material was packed into a fluidized bed drier and dried at 50° C. for 4 hours. X-ray analysis of the dried material showed it to be GTF form W. Example 5

Preparation of GTF Form X

A 1-liter reactor equipped with mechanical stirrer, condenser and thermometer, was charged with 1-cyclopropyl-6,7-difluoro-1.4-dihydro-8-methoxy-4-oxo-3-quinolinecarboxylic acid (40 g), dimethylsulfoxide (DMSO) (800 ml) and 2-methylpiperazine (28.5 g). The reaction mixture was then heated to 55° C. and stirred for 24 hours until completion of the reaction.

Toluene and $H_2O$ (2.5:1, v:v) were added in a total volume of 280 mL at 55° C. The mixture was then cooled to 5° C. over 4 hours, maintained at 5° C. for 20 hours, heated again to 35° C., maintained at 35° C. for 1 hour. This thermal history (profile) was repeated from 35° C., viz., cooling over 4 hours to 5° C., maintaining the temperature for 1 hour and heating to 35° C. over 1 hour. The mixture was maintained at 35° C. for 1 hour and cooled to 10° C. over 6 hours. The resulting suspension was then maintained at 10° C. for 12 hours.

The suspension was suction filtered and washed with acetonitrile (30 mL). The wet sample was analyzed by XRD analysis and found to be gatifloxacin form X.

Example 6

Preparation of Gatifloxacin Form Y

Gatifloxacin-HCl (10 g) was suspended in 60 mL of a mixture of acetonitrile:$H_2O$ (90:10). The suspension was cooled to 5° C. At this an aqueous solution of NaOH 47% (0.7 eq) was added to neutralize the hydrochloride. The mixture was stirred at 5° C. for 1 hour and then the precipitate was collected by filtration and washed with the aqueous mixture (10 mL) ACN:$H_2O$ (90:10). The solid was dried under vacuum at 50° C. overnight. The solid was analyzed by XRD and found to be form Y.

Example 7

Preparation of Gatifloxacin Form Z

A 100 mL reactor was charged with 9.4 g of gatifloxacin and acetonitrile (ACN; 86 ml). Hyflo (5%) was added and the suspension refluxed for 15 min. The solution was filtered hot through a glass frit into a clean, warmed reactor to obtain a hot-filtered solution. The clear solution was then cooled to 60° C. over 30 minutes, maintained at 60° C. for 1 hour, cooled to 5° C. over 2.5 hours and maintained at this temperature for 30 minutes. During the cooling step to 5° C., a precipitate began to appear at 34° C. After the end of the cooling profile the precipitated was collected and wash with 10 mL of ACN. The wet sample was analyzed by XRD and found to be form Z.

Example 8

Preparation of Gatifloxacin Form CH1

Gatifloxacin (0.5 g) form CY was heated to 100° C. for 30 minutes. The resulting sample was then analyzed by XRD and found to be form CH1.

Example 9

Preparation of Gatifloxacin Form CH2

1. Gatifloxacin form V (0.5 g) was heated to 65° C. for 15 minutes. The resulting sample was then analyzed by XRD, and found to contain a mixture of gatifloxacin form V and form CH2.

2. Gatifloxacin pentahydrate (0.5 g) was heated to 100° C. for 30 minutes. The resulting sample was then analyzed by XRD, and found to have gatifloxacin form CH2 content.

3. Gatifloxacin form CW (0.5 g) was heated to 100° C. for 30 minutes. The resulting sample was then analyzed by XRD and found to have gatifloxacin form CH2 content.

4. Gatifloxacin form Ω (3 g) was heated to 40° C. at 75% of relative humidity for 3 months. The resulting sample was then analyzed by XRD and found to contain a mixture of gatifloxacin form Ω and form CH2.

Example 11

Preparation of Gatifloxacin Form RH

Gatifloxacin form R (0.5 g) was heated to 60° C. for 30 minutes. The resulting sample was then analyzed by XRD, and found to contain the novel gatifloxacin form RH.

Example 12

Preparation of Gatifloxacin Form V

Gatifloxacin form CZ (0.5 g) was heated to 120° C. for 30 minutes. The resulting sample was then analyzed by XRD, and found to contain the novel gatifloxacin form V.

Example 13

Preparation of Gatifloxacin Form T2RP

Gatifloxacin form CW (0.5 g) was heated to 140° C. for 30 minutes. The resulting sample was then analyzed by XRD, and found to contain the T2RP form of gatifloxacin.

Example 14

Preparation of Gatifloxacin Form HX1

A 250 mL reactor was charged with 30 g of the wet material obtained after the chemical reaction as described in examples 1 and 2 at ambient temperature with 150 mL of water. The suspension was stirred at ambient temperature for 1 hour and the solid was isolated by filtration and washed with water (60 mL).

Example 15

Preparation of Gatifloxacin Form HX2

A 250 mL reactor was charged with 30 g of the wet material obtained after the chemical reaction as described in examples 1 and 2 at ambient temperature with 150 mL of water. The suspension was stirred at this temperature for 3 hours and the solid was collected by filtration and washed with water (60 mL).

We claim:

1. A method of making crystalline gatifloxacin form CX characterized by at least one of: (i) a powder x-ray diffraction pattern having reflections at about 6.5, 14.6, 17.4, and 19.4°±0.2° 2θ; and (ii) a differential scanning calorimetry thermogram having endothermic peaks at about 122° C. and about 137° C., comprising the steps of:
   a) combining an initial solution of gatifloxacin in DMSO with water at a temperature of about 55° C.,
   b) cooling the combination to a temperature of about 0° C. at a cooling rate of about 10° per hour whereby a suspension is obtained,
   c) isolating the crystalline gatifloxacin form CX from the suspension, and
   d) washing the isolated crystalline gatifloxacin form CX with acetonitrile.

2. A method of making crystalline gatifloxacin form CW characterized by at least one of: (i) a powder x-ray diffraction pattern having reflections at about 5.2, 11.2, 11.5, 14.3, and 22.2°±0.2° 2θ; and (ii) a differential scanning calorimetry thermogram having an endothermic peak at about 178° C., comprising the steps of:
   a) providing crystalline gatifloxacin form CX characterized by at least one of: (i) a powder x-ray diffraction pattern having reflections at about 6.5, 14.6, 17.4, and 19.4°±0.2° 2θ; and (ii) a differential scanning calorimetry thermogram having endothermic peaks at about 122° C. and about 137° C., and
   d) drying the crystalline gatifloxacin form CX at reduced pressure for about 8 hours to obtain the crystalline gatifloxacin form CW.

3. The method of claim 2 further comprising the step of, prior to drying, washing the isolated solid gatifloxacin with acetonitrile.

\* \* \* \* \*